US006265163B1

(12) United States Patent
Albrecht et al.

(10) Patent No.: US 6,265,163 B1
(45) Date of Patent: Jul. 24, 2001

(54) SOLID PHASE SELECTION OF DIFFERENTIALLY EXPRESSED GENES

(75) Inventors: Glenn Albrecht, Redwood City, CA (US); Sydney Brenner, Cambridge (GB); Robert B. DuBridge, Belmont, CA (US)

(73) Assignee: Lynx Therapeutics, Inc., Hayward, CA (US)

( * ) Notice: Subject to any disclaimer, the term of this patent is extended or adjusted under 35 U.S.C. 154(b) by 25 days.

(21) Appl. No.: 09/130,546

(22) Filed: Aug. 6, 1998

Related U.S. Application Data

(63) Continuation-in-part of application No. 09/005,222, filed on Jan. 9, 1998, now abandoned.

(51) Int. Cl.⁷ ...................................................... C12Q 1/68
(52) U.S. Cl. ................................ 435/6; 435/5; 536/24.31; 536/24.32; 536/25.32
(58) Field of Search ........................ 435/5, 6; 536/24.31, 536/24.32, 25.32

(56) References Cited

U.S. PATENT DOCUMENTS

| | | | |
|---|---|---|---|
| 3,710,933 | 1/1973 | Fulwyler | 209/3 |
| 4,354,114 | 10/1982 | Karnaukhov | 250/458.1 |
| 4,791,355 | 12/1988 | Coulter | 324/71.1 |

(List continued on next page.)

FOREIGN PATENT DOCUMENTS

| | | |
|---|---|---|
| 0303459 A2 | 2/1989 | (EP) . |
| 0 392 546 A2 | 10/1990 | (EP) . |
| 0799897A1 | 10/1997 | (EP) . |
| WO90/06042 | 6/1990 | (WO) . |
| WO 93/06121 | 4/1993 | (WO) . |
| WO93/17126 | 9/1993 | (WO) . |
| WO95/21944 | 8/1995 | (WO) . |
| WO95/35505 | 12/1995 | (WO) . |
| WO 96/12039 | 4/1996 | (WO) . |
| WO96/12014 | 4/1996 | (WO) . |
| WO96/41011 | 12/1996 | (WO) . |
| WO97/43450 | 11/1997 | (WO) . |
| WO 98/26098 | 6/1998 | (WO) . |

OTHER PUBLICATIONS

Lisitsyn et al, Cloning the differences between two complex genomes, Science, 259: 946–951 (1993).

Koss et al, "Flow cytometric measurements of DNA and other cell components in human tumors: a critical appraisal," Human Pathology, 20: 528–548 (1989).

Van Ness et al, "A versatile solid support system for oligodeoxynucleotide probe–based hybridization assays," Nucleic Acids Research, 19: 3345–3350 (1991).

Fulton et al, "Advanced multiplexed analysis iwth the Flow-Metrix™ system," Clinical Chemistry, 43: 1749–1756 (1997).

(List continued on next page.)

*Primary Examiner*—Jezia Riley
(74) *Attorney, Agent, or Firm*—Stephen C. Macevicz

(57) ABSTRACT

The invention provides a method and materials for monitoring and isolating differentially expressed genes. In accordance with the method of the invention, differently labeled populations of DNAs from sources to be compared are competitively hybridized with reference DNA cloned on solid phase supports, e.g. microparticles, to provide a differential expression library which, in the preferred embodiment, may be manipulated by fluorescence-activated cell sorting (FACS). Monitoring the relative signal intensity of the different fluoresent labels on the microparticles permits quantitative analysis of expression levels relative to the reference DNA. Populations of microparticles having relative signal intensities of interest can be isolated by FACS and the attached DNAs identified by sequencing, such as with massively parallel signature sequencing (MPSS), or with conventional DNA sequencing protocols.

16 Claims, 9 Drawing Sheets

U.S. PATENT DOCUMENTS

| | | | |
|---|---|---|---|
| 4,812,394 | 3/1989 | Dolbeare et al. | 435/6 |
| 4,837,168 | 6/1989 | de Jaeger | 436/533 |
| 4,921,805 | 5/1990 | Gebeyehu | 435/270 |
| 5,028,545 | 7/1991 | Soini | 436/501 |
| 5,104,791 | 4/1992 | Abbott | 435/6 |
| 5,173,260 | 12/1992 | Zander | 422/57 |
| 5,206,143 | 4/1993 | Horan | 435/7.24 |
| 5,445,394 | 8/1995 | Dussere-Telmon et al. | 435/6 |
| 5,478,893 | 12/1995 | Ghosh | 525/329.4 |
| 5,510,270 | 4/1996 | Fodor et al. | 432/518 |
| 5,518,883 | 5/1996 | Soini | 435/6 |
| 5,567,627 | 10/1996 | Lehnen | 436/518 |
| 5,604,097 | 2/1997 | Brenner | 436/518 |
| 5,629,147 * | 5/1997 | Asgari et al. | 435/5 |
| 5,656,462 | 8/1997 | Kellar et al. | 435/91.2 |
| 5,658,736 | 8/1997 | Wong | 435/6 |
| 5,663,242 | 9/1997 | Ghosh | 525/329.4 |
| 5,721,098 | 2/1998 | Pinkel | 435/6 |
| 5,736,330 | 4/1998 | Fulton | 435/6 |
| 5,736,332 | 4/1998 | Mandecki | 435/6 |
| 5,800,992 | 9/1998 | Fodor | 435/6 |
| 5,830,645 | 11/1998 | Pinkel | 435/6 |
| 6,013,449 | 1/2000 | Hacia | 435/6 |
| 6,060,240 | 5/2000 | Kamb | 435/6 |

OTHER PUBLICATIONS

Hakala et al, "Time–resolved fluorescence detection of oligonucleotide hybridization on a single microparticle: covalent immobilization of oligonucleotides and quantitation of a model system," Bioconjugate Chemistry, 8: 232–237 (1997).

Hakala et al, "Detection of oligonucleotide hybridization on a single microparticle by time–resolved fluorometryL hybridization assays on polymer particles obtained by direct solid phase assembly of the oligonucleotide probes," Bioconjugate Chemistry, 8: 378–384 (1997).

Raineri et al, "Improved efficiency for single–sided PCR by creating a reusable pool of first–strand cDNA coupled to a solid phase," Nucleic Acids Research, 19:4010 (1991).

Lee et al, "Reusable cDNA libraries coupled to magnetic beads," Anal. Biochem., 206: 206–207 (1992).

Lovgren et al, "Sensitive bioaffinity assays with individual microparticles and time–resolved fluorometry," Clinical Chemistry, 43: 1937–1943 (1997).

Product brochure, "Dynabeads template preparation kit," Dynal Inc. (Great Neck, New York), 1991.

Vlieger et al, "Quantitation of polymerase chain reaction products by hybridizaton–based assays with fluorescent, colorimetric, or chemiluminscent detection," Anal. Biochem., 205: 1–7 (1992).

Khudyakov et al, "Primer specific solid–phase detection of PCR products,"Nucleic Acids Research, 22: 1320–1321 (1994).

Wan et al, "Cloning differentially expressed mRNAs," Nature Biotechnology, 14: 1685–1691.

Stamm et al, "Sanchored PCR: PCR with cDNA coupled to a solid phase," Nucleic Acids Research, 19: 1350 (1991).

Beattie et al, "Advances in genosensor research, " Clin. Chem., 41(5): 700–706 (1995).

Sagerstrom et al, "Subtractive cloning: past, present, and future," Annu. Rev. Biochem., 66: 751–783 (1997).

Yershov et al, "DNA analysis and diagnostics on oligonucleotide microchips," Proc. Natl. Acad. Sci., 93: 4913–4918 (1996).

Chee et al, "Accessing genetic information with high–density DNA arrays,"Science, 274: 610–614 (1996).

Lipshutz et al, "Using oligonucleotide probe arrays to access genetic diversity," BioTechniques, 19: 442–447 (1995).

Shalon et al, "A DNA microarray system for analyzing complex DNA samples using two–color fluorescent probe hybirdization," Genome Research, 6: 639–645 (1996).

Schena et al, "Quantitative monitoring of gene expression patterns with a complementary DNA microarray," Science, 270: 467–470 (1995).

DeRisi et al, "Exploring the metabolic and genetic control of gene expression on a genomic scale," Science, 278: 680–686 (1997).

Zhao et al, "High–density cDNA filter analysis: a novel approach for large–scale, quantitative analysis of gene expression," Gene, 156: 207–213 (1995).

Wodicka et al, "Genome–wide expression monitoring in *Saccharomyces cerevisiae*," Nature Biotechnology, 15: 1359–1367 (1997).

Shoemaker et al, "Quantitative phenotypic analysis of yeast deletion mutants using a highly parallel molecular bar–coding strategy," Nature Genetics, 14: 450–456 (1996).

Unrau et al, "Non–cloning amplification of specific DNA fragments from whole genomic DNA digests using DNA 'indexers,'" Gene, 145: 163–169 (1994).

Broude et al, "Enhanced DNA sequencing by hybridization," Proc. Natl. Acad. Sci., 91: 3072–3076 (1994).

Hultman et al, "Direct solid phase sequencing of genomic and plasmid DNA using magnetic beads as solid support," Nucleic Acids Research, 17: 4937–4946 (1989).

Hensel et al, "Simultaneous identification of bacterial virulence genes by negative selection," Science, 269: 400–403 (1995).

Needels et al, "Generation and screening of an oligonucleotide–encoded synthetic peptide library," Proc. Natl. Acad. Sci., 90: 10700–10704 (1993).

* cited by examiner

SOLID PHASE SELECTION OF DIFFERENTIALLY EXPRESSED GENES

This is a continuation-in-part of co-pending U.S. patent application Ser. No. 09/005,222 filed Jan. 9, 1998, which application is incorporated by reference.

FIELD OF THE INVENTION

The invention relates generally to methods for identifiing differentially expressed genes, and more particularly, to a method of competitively hybridizing differentially expressed DNAs with reference DNA sequences cloned on solid phase supports to provide a differential expression library which can be physically manipulated, e.g. by fluorescence-activated flow sorting.

BACKGROUND

The desire to decode the human genome and to understand the genetic basis of disease and a host of other physiological states associated differential gene expression has been a key driving force in the development of improved methods for analyzing and sequencing DNA, Adams et al, Editors, Automated DNA Sequencing and Analysis (Academic Press, New York, 1994). Current genome sequencing projects use Sanger-based sequencing technologies, which enable the sequencing and assembly of a genomes in the size range of 2–4 megabases with about 24 man-months of effort, e.g. Fleischmann et al, Science, 269: 496–512 (1995). Such a genome is about 0.005 the size of the human genome, which is estimated to contain about $10^5$ genes, 15% of which—or about 3 megabases-are active in any given tissue. The large numbers of expressed genes make it difficult to track changes in expression patterns by direct sequence analysis. More commonly, expression patterns are analyzed by lower resolution techniques, such as differential display, indexing, subtraction hybridization, or one of the numerous DNA fingerprinting techniques, e.g. Lingo et al, Science, 257: 967–971 (1992); Erlander et al, International patent application PCT/US94/13041; McClelland et al, U.S. Pat. No. 5,437,975; Unrau et al, Gene, 145: 163–169 (1994); Sagerstrom et al, Annu. Rev. Biochem. 66: 751–783 (1997); and the like. For the techniques that result in the isolation of a subset of DNA sequences, sequencing of randomly selected clones is typically carried out using conventional Sanger sequencing; thus, the scale of the analysis is limited.

Recently, several higher resolution techniques have been reported that attempt to provide direct sequence information for analyzing patterns of gene expression on a large scale: Schena et al, Science, 270: 467–469 (1995), and DeRisi et al, Science, 278: 680–686 (1997), report the hybridization of mRNAs to a collection of cDNAs arrayed on a glass slide; Velculescu et al, Science, 270: 484–486 (1995) report the excision and concatenation of short segments of sequence adjacent to type iHs restriction sites from members of a cDNA library, followed by Sanger sequencing of the concatenated segments to give a profile of sequences in the library; and Wodicka et al, Nature Biotechnology, 15: 1359–1367 (1997), report genome-wide expression monitoring of yeast under different growth conditions using high density oligonucleotide arrays containing hybridization sites for each of the more than 6000 genes of the organism. While these techniques represent tremendous progress in expression analysis, they still have drawbacks which limit their widespread application to many expression monitoring problems. For example, in both the techniques of Schena and Wodicka, the sequences being monitored must be known beforehand, and in the case of Wodicka preferably the entire complement of an organism's genes must be known. In the technique of Schena, there are significant problems in constructing arrays containing a substantial portion, e.g. ten thousand, or more, of genes whose expression may be relevant, as cDNAs of each gene are separately prepared an applied to an array and currently available arrays are typically not re-usable leading to standardization and quality control issues when multiple measurements over time are desired. In the technique Velculescu, even though the sequencing burden is reduced, as with any random sequencing approach, abundant non-differentially expressed genes are sequenced repeatedly—at the expense of obtaining expression information on differentially regulated genes, and it is not clear from the reported data whether the technique is capable of providing sample sizes sufficiently large to permit the reliable expression profiling of genes that are expressed very low levels, e.g. Kollner et al, Genomics, 23: 185–191 (1994).

In view of the above, it would be highly desirable if a technique were available for monitoring differential gene expression that had the capability of massively parallel analysis of all or a substantial fraction of expressed genes, but was free of the shortcomings of current techniques.

SUMMARY OF THE INVENTION

Accordingly, objects of our invention include, but are not limited to, providing a method for identifying and isolating differentially expressed genes or polymorphic genes; providing a method of identifying and isolating polynucleotides on the basis of labels that generate different optical signals; providing a method for profiling gene expression of large numbers of genes simulaneously or identifying large numbers of polymorpbic genes simultaneously; providing a method of identifying and separating genes in accordance with whether their expression is increased or decrease under any given conditions; and providing a method for massively parallel signature sequencing of large numbers of genes isolated according to their expression characteristics or according to whether they contain a polymorphic sequence.

Our invention accomplishes these and other objects by providing differently labeled populations of DNAs from cell or tissue sources whose gene expression is to be compared. In comparing gene expression, differently labeled DNAs of a plurality of populations are competitively hybridized with reference DNA cloned on solid phase supports. Preferably, the solid phase supports are microparticles which, after such competitive hybridization, provide a differential expression library which may be manipulated by fluorescence-activated cell sorting (FACS), or other sorting means responsive to optical signals generated by labeled DNA on the microparticles. Monitoring the relative signal intensity of the different labels on the microparticles permits quantification of the relative expression of particular genes in the different populations.

In one aspect of the invention, populations of microparticles having relative signal intensities of interest are isolated by FACS and the attached DNAs are sequenced to determine the identities of the differentially expressed genes.

Preferably, the method of the invention is carried out by the following steps: a) providing a reference DNA population of DNA sequences attached to separate solid phase supports in clonal subpopulations; b) providing a population of polynucleotides of expressed genes from each of the plurality of different cells or tissues, the polynucleotides of expressed genes from different cells or tissues having a different light-generating label and the polynucleotides of expressed genes from the same cells or tissues having the same light-generating label; c) competitively hybridizing the populations of polynucleotides of expressed genes from each of the plurality of different cells or tissues with the reference DNA population to form duplexes between the DNA sequences of the reference DNA population and polynucleotides of each of the different cells or tissues such that the polynucleotides are present in duplexes on each of the solid phase supports in ratios directly related to the relative expression of their corresponding genes in the different cells or tissues; and d) sorting each solid phase support according to a relative optical signal generated by the light-generating labels of the duplexes attached thereto. Preferably, the reference DNA population is derived from genes of the plurality of different cells or tissues being analyzed. As used herein, the phrase "polynucleotides of expressed genes" is meant to include any RNA produced by transcription, including in particular M/RNA, and DNA produced by reverse transcription of any RNA, including in particular cDNA produced by reverse transcription of M/RNA.

The present invention overcomes shortcoming in the art by providing a means for separating and identifying genes that are differentially expressed without requiring any previous analysis or knowledge of the sequences. The invention also permits differentially regulated genes to be separated from unregulated genes for analysis, thereby eliminating the need to analyze large numbers of unregulated genes in order to obtain information on the genes of interest.

DEFINITIONS

Figure 1A:
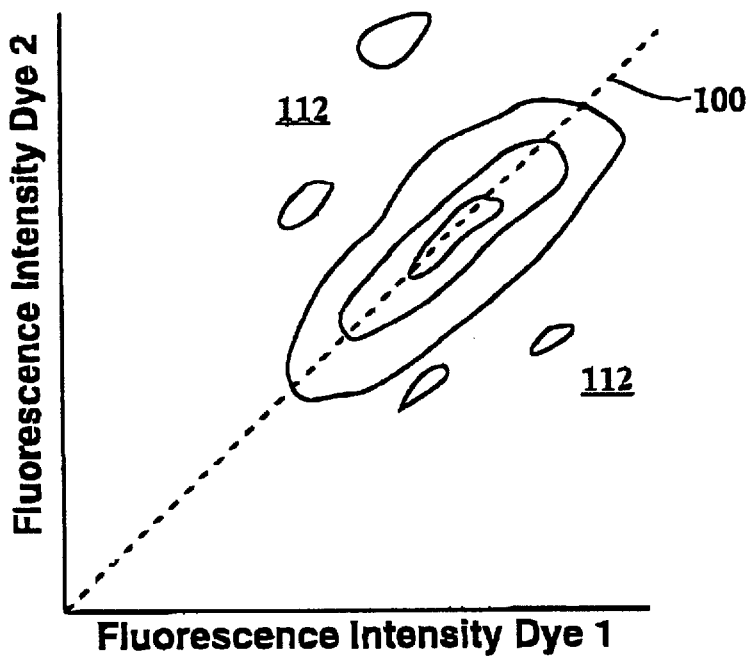
FIGS. 1a and 1b illustrate FACS analysis of microparticles loaded with competitively hybridized DNA strands labeled with two different fluorescent dyes.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by ennymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand The term also comprehends the pairing of nucleoside analogs, such as deoxyinosine, nucleosides with 2-amninopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl (forms, e.g. as described in Kornberg and Baker, DNA Replication, 2nd Ed. (Freeman,) San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . ." so that its sequence is represented as a binary code, e.g. "100101 . . . " for "C—(not C)—(not C)—C—(not C)—C . . . " and the like.

As used herein, the term "complexity" in reference to a population of polynucleotides means the number of different species of polynucleotide present in the population.

As used herein, the term "relative gene expression" or "relative expression" in reference to a gene refers to the relative abundance of the same gene expression product, usually an mRNA, in different cells or tissue types.

DETAILED DESCRIPTION OF THE INVENTION

The present invention provides a means for analyzing relative gene expression in a plurality of cells and/or tissues that are of interest. The plurality usually comprises a pair of cell or tissue types, such as a diseased tissue or cell type and a healthy tissue or cell type, or such as a cell or tissue type being subjected to a stimulus or stress, e.g. a change of nutrients, temperature, or the like, and the corresponding cell or tissue type in an unstressed or unstinulated state. The plurality may also include more than two cell or tissue types, such as would be required in a comparison of expression patterns of the same cell or tissue over time, e.g. liver cells after exposure of an organism to a candidate drug, organ cells of a test animal at different developmental states, and the like. Preferably, the plurality is 2 or 3 cell or tissue types; and more preferably, it is 2 cell or tissue types. For analysis in accordance with the invention, messenger RNA (mRNA) is extracted from the cells or tissues of interest using conventional protocols, as disclosed in, for example, Sambrook et al, Molecular Cloning: A Laboratory Manual, 2nd Edition (Cold Spring Harbor Laboratory, New York). Preferably, the populations of mRNAs to be compared are converted into populations of labeled cDNAs by reverse transcription in the presence of a labeled nucleoside triphosphate using conventional protocols, e.g. Schena et al, Science 270: 467–470 (1995); DeRisi et al, Science 278: 680–686 (1997); or the like, prior to hybridization to a reference DNA population.

An important feature of the invention is that the genes whose expression levels change or are different than those of the other cells or tissues being examined may be analyzed separately from those that are not regulated or otherwise altered in response to whatever stress or condition is being studied. As described below, in the preferred embodiment gene products from the cells or tissues of interest are competitively hybridized with a reference DNA population consisting of DNA sequences attached in clonal subpopulations to separate microparticles. The microparticles carrying labeled gene products in ratios indicating differential expression may be manipulated and analyzed separately from those carrying labeled gene products in ratios indicating no change in expression, e.g. "house-keeping" genes, genes encoding structural proteins, or the like.

Another important feature of the invention is that the identity of the gene products being analyzed, e.g. cDNA, M/RNA, RNA transcript, or the like, need not be known prior to analysis. After relative expression is determined, cDNAs derived from expressed genes may be identefed by direct sequencing on the solid phase support, preferably a mniroparticle, using a number of different sequencing approaches. For identifcal, only a portion of the cDNAs need be sequenced. In many cases, the portion may be as small as nine or ten nucleotides, e.g. Velculescu et al (cited above). Preferably, entire subpopulations of differentially expressed genes are sequenced simultaneously using MPSS, or a similar parallel analysis technique. In a preferred embodiment, this is conveniently accomplished by providing a reference DNA population of DNA sequences such that each such sequence is attached to a separate microparticle in a clonal subpopulation. As explained more fuilly below, clonal subpopulations are preferably formed by so-called "solid phase cloning" disclosed in Brenner, U.S. Pat. No. 5,604,097 and Brenner et al, International patent application PCT/96/09513. Briefly, such clonal subpopulations are formed by hybridizing an amplified sample of tag-cDNA conjugates onto one or more solid phase support(s), e.g. separate microparticles, so that individual microparticles, or different regions of a larger support, have attached multiple copies of the same cDNA. The number of copies of a cDNA in a clonal subpopulation may vary widely in different embodiments depending on several factors, including the density of tag complements on the solid phase supports, the size and composition of microparticle used, the duration of hybridization reaction, the complexity of the tag repertoire, the concentration of individual tags, the tag-cDNA sample size, the labeling means for generating optical signals, the particle sorting means, signal detection system, and the like. Guidance for making design choices relating to these factors is readily available in the literature on flow cytometry, fluorescence microscopy, molecular biology, hybridization technology, and related disciplines, as represented by the references cited herein. Preferably, the number of copies of a cDNA in a clonal subpopulation is sufficient to permit FACS sorting of microparticles, wherein fluorescent signals are generated by one or more fluorescent dye molecules carried by the cDNAs attached to the microparticles. Typically, this number can be as low as a few thousand, e.g. 3–5,000, when a fluorescent molecule such as fluorescein is used, and as low as several hundred, e.g. 800–8000, when a rhodamine dye, such as rhodamine 6G, is used. More preferably, when loaded microparticles are sorted by FACS, clonal subpopulations consist of at least $10^4$ copies of a cDNA; and most preferably, in such embodiments, clonal subpopulations consist of at least $10^5$ copies of a cDNA.

Labeled cDNAs or RNAs from the cells or tissues to be compared are competitively hybridized to the DNA sequences of the reference DNA population using conventional hybridization conditions, e.g. such as disclosed in Schena et al (cited above); DeRisi et al (cited above); or Shalon, Ph.D. Thesis entitled "DNA Microarrays," Stanford University (1995). After hybridization, an optical signal is generated by each of the two labeled species of cDNAs or RNAs so that a relative optical signal is determined for each microparticle. Preferably, such optical signals are generated and measured in a fluorescence activated cell sorter, or like instrument, which permits the microparticles to be sorted and accumulated whose relative optical signal fall within a predetermined range of values. The microparticles loaded with cDNAs or RNAs generating relative optical signals in the desired range may be isolated and identified by sequencing, such as with MPSS, as described more fully below.

Figure 3A:
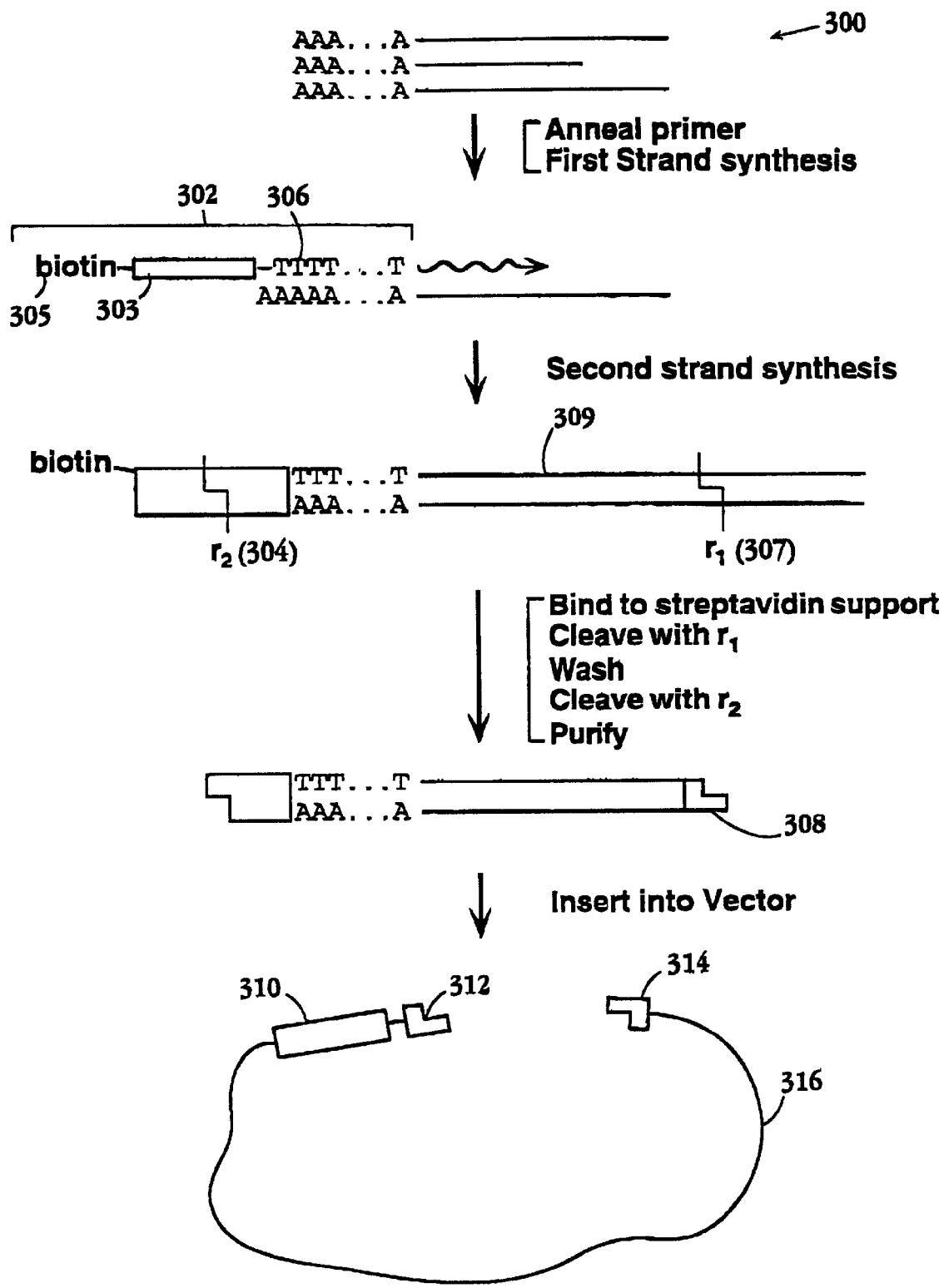
FIG. 3a illustrates a preferred scheme for converting isolated messenger RNA (M/RNA) into cDNA and insertion of the cDNA into a tag-containing vector.
Figure 3B:
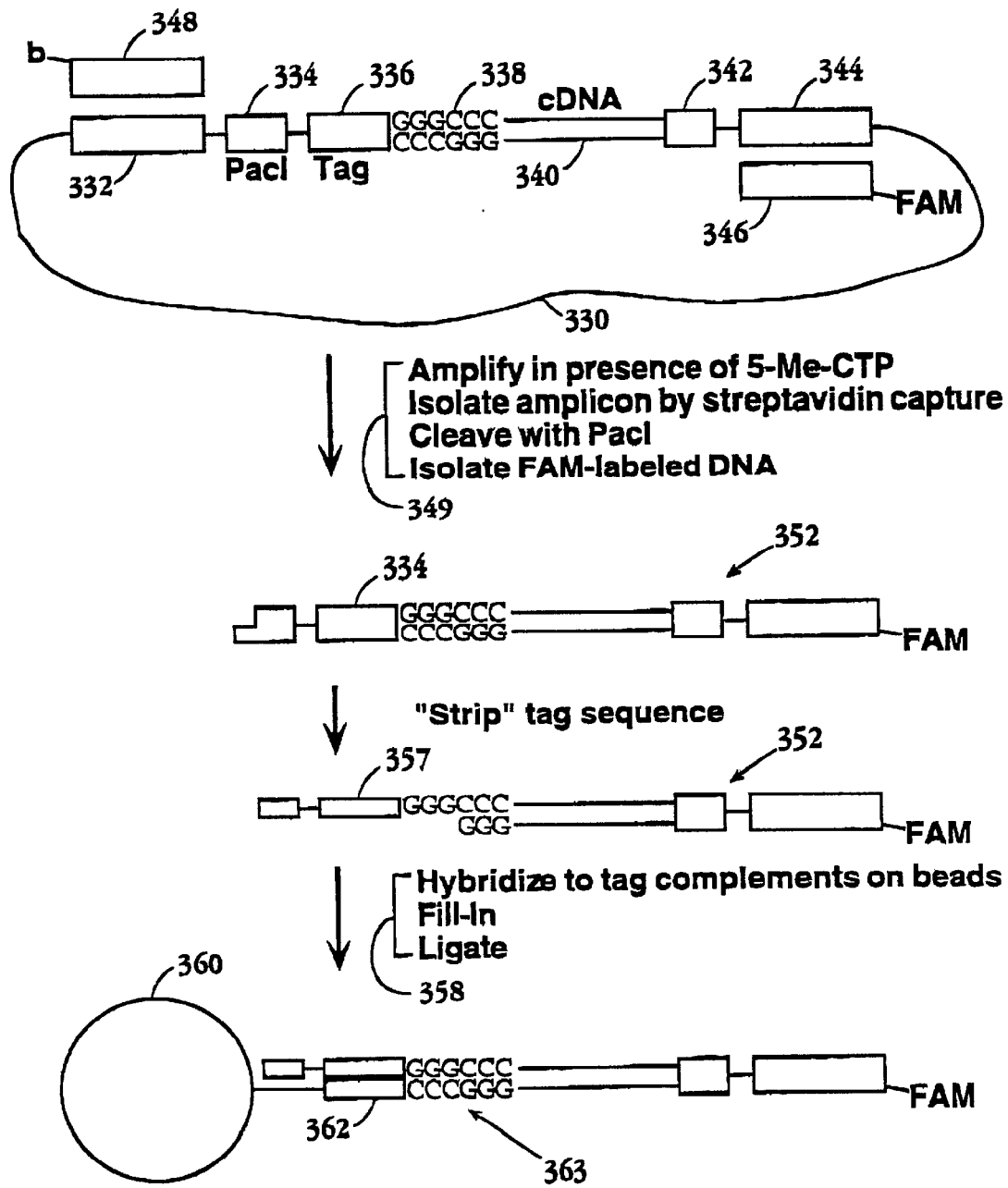
FIG. 3b illustrates a preferred scheme for amplifying tag-cDNA conjugates out of a vector and loading the amplified conjugates onto microparticles.

Preferably, clonal subpopulations of cDNAs are attached to microparticles using the processes illustrated in FIGS. 3a and 3b. First, as illustrated in FIG. 3a, mRNA (300) is extracted from a cell or tissue source of interest using conventional techniques and is converted into cDNA (309)

with ends appropriate for inserting into vector (316). Preferably, primer (302) having a 5' biotin (305) and poly (dT) region (306) is annealed to mRNA strands (300) so that the first strand of cDNA (309) is synthesized with a reverse transcriptase in the presence of the four deoxyribonucleoside triphosphates. Preferably, 5-methyldeoxycytidine triphosphate is used in place of deoxycytosine triphosphate in the first strand synthesis, so that cDNA (309) is hemimethylated, except for the region corresponding to primer (302). This allows primer (302) to contain a non-methylated restriction site for releasing the cDNA from a support. The use of biotin in primer (302) is not critical to the invention and other molecular capture techniques, or moieties, can be used, e.g. triplex capture, or the like. Region (303) of primer (302) preferably contains a sequence of nucleotides that results in the formation of restriction site $r_2$ (304) upon synthesis of the second strand of cDNA (309). After isolation by binding the biotinylated cDNAs to streptavidin supports, e.g. Dynabeads M-280 (Dynal, Oslo, Norway), or the like, cDNA (309) is preferably cleaved with a restriction endonuclease which is insensitive to hemimethylation (of the C's) and which recognizes site $r_1$, (307). Preferably, $r_1$, is a four-base recognition site, e.g. corresponding the Dpn II, or like enzyme, which ensures that substantially all of the cDNAs are cleaved and that the same defined end is produced in all of the cDNAs. After washing, the cDNAs are then cleaved with a restriction endonuclease recognizing $r_2$, releasing fragment (308) which is purified using standard techniques, e.g. ethanol precipitation, polyacrylamide gel electrophoresis, or the like. After resuspending in an appropriate buffer, fragment (308) is directionally ligated into vector (316), which carries tag (310) and a cloning site with ends (312) and (314). Preferably, vector (316) is prepared with a "stuffer" fragment in the cloning site to aid in the isolation of a fully cleaved vector for cloning.

After formation of a library of tag-cDNA conjugates, a sample of host cells is plated to determine the number of recombinants per unit volume of culture medium. The size of sample taken for further processing depends on the size of tag repertoire used in the library construction. As taught by Brenner et al, International application PCT/US96/09513 and U.S. Pat. No. 5,604,097, which is incorporated by reference, a sample preferably includes a number of conjugates equivalent to about one percent the size of the tag repertoire in order to minimize the selection of "doubles," ie. two or more conjugates carrying the same tag and different cDNAs. Thus, for a tag repertoire consisting of a concatenation of eight 4-nucleotide "words" selected from a minimally cross-hybridizing set of eight words, the size of the repertoire is $8^8$, or about $1.7 \times 10^7$ tags. Accordingly, with such a repertoire, a sample of about $1.7 \times 10^5$ conjugate-containing vectors is preferably selected for amplification and further processing as illustrated in FIG. 3b.

Preferably, tag-cDNA conjugates are carried in vector (330) which comprises the following sequence of elements: first primer binding site (332), restriction site $r_3$ (334), oligonucleotide tag (336), junction (338), cDNA (340), restriction site $r_4$ (342), and second primer binding site (344). After a sample is taken of the vectors containing tag-cDNA conjugates the following steps are preferably implemented: The tag-cDNA conjugates are preferably amplified from vector (330) by use of biotinylated primer (348) and labeled primer (346) in a conventional polymerase chain reaction (PCR) in the presence of 5-methyldeoxycytidine triphosphate, after which the resulting amplicon is isolated by streptavidin capture. Restriction site $r_3$ preferably corresponds to a rarecutting restriction endonuclease, such as Pac I, Not I, Fse I, Pme I, Swa I, or the like, which permits the captured amplicon to be release from a support with minimal probability of cleavage occurring at a site internal to the cDNA of the amplicon. Junction (338) which is illustrated as the sequence:

```
5'... GGGCCC ...
3'... CCCGGG ...
``` causes the DNA polymerase "stripping" reaction to be halted at the G triplet, when an appropriate DNA polymerase is used with dGTP. Briefly, in the "stripping" reaction, the 3'→5' exonuclease activity of a DNA polymerase, preferably T4 DNA polymerase, is used to render the tag of the tag-cDNA conjugate single stranded, as taught by Brenner, U.S. Pat. No. 5,604,097; and Kuijper et al, Gene, 112: 147–155 (1992). In the preferred embodiment where sorting is accomplished by formation of duplexes between tags and tag complements, tags of tag-cDNA conjugates are rendered single standed by first selecting words that contain only three of the four natural nucleotides, and then by preferentially digesting the three nucleotide types from the tag-cDNA conjugate in the 3'→5' direction with the 3'→5' exonuclease activity of a DNA polymerase. In the preferred embodiment, oligonucleotide tags are designed to contain only A's, G's, and T's; thus, tag complements (including that in the double stranded tag-cDNA conjugate) consist of only A's, C's, and T's. When the released tag-cDNA conjugates are treated with T4 DNA polymerase in the presence of dGTP, the complementary strands of the tags are "stripped" away to the first G. At that point, the incorporation of dG by the DNA polymerase balances the exonuclease activity of the DNA polymerase, effectively halting the "stripping" reaction. From the above description, it is clear that one of ordinary skill could make many alternative design choices for carrying out the same objective, i.e. rendering the tags single stranded. Such choices could include selection of different enzymes, different compositions of words making up the tags, and the like.

When the "stripping" reaction is quenched, the result is duplex (356) with single stranded tag (357). After isolation, steps (358) are implemented: the tagcDNA conjugates are hybridized to tag complements attached to microparticles, a fill-in reaction is carried out to fill any gap between the complementary strand of the tag-cDNA conjugate and the 5' end of tag complement (362) attached to microparticle (360), and the complementary strand of the tag-cDNA conjugate is covalently bonded to the 5' end (363) of tag complement (362) by treating with a ligase. This embodiment requires, of course, that the 5' end of the tag complement be phosphorylated, e.g. by a kinase, such as, T4 polynucleotide kinase, or the like. The fill-in reaction is preferably carried out because the "stripping" reaction does not always halt at the first G. Preferably, the fill-in reaction uses a DNA polymerase lacking 5'→3' exonuclease activity and strand displacement activity, such as T4 DNA polymerase. Also preferably, all four dNTPs are used in the fill-in reaction, in case the "stripping" extended beyond the G triplet.

As explained firther below, the tag-cDNA conjugates are hybridized to the full repertoire of tag complements. That is, among the population of microparticles, there are microparticles having every tag sequence of the entire repertoire. Thus, the tag-cDNA conjugates will hybridize to tag complements on only about one percent of the microparticles. Microparticles to which tag-cDNA have been hybridized are referred to herein as "loaded microparticles." For greater efficiency, loaded microparticles are preferably separated from unloaded microparticles for further processing. Such separation is conveniently accomplished by use of a fluorescence-activated cell sorter (FACS), or similar instrument that permits rapid manipulation and sorting of large numbers of individual microparticles. In the embodiment illustrated in FIG. 3b, a fluorescent label, e.g. FAM (a fluorescein derivative, Haugland, Handbook of Fluorescent Probes and Research Chemicals, Sixth Edition, (Molecular Probes, Eugene, Oreg., 1996)) is attached by way of primer (346).

Figure 3C:
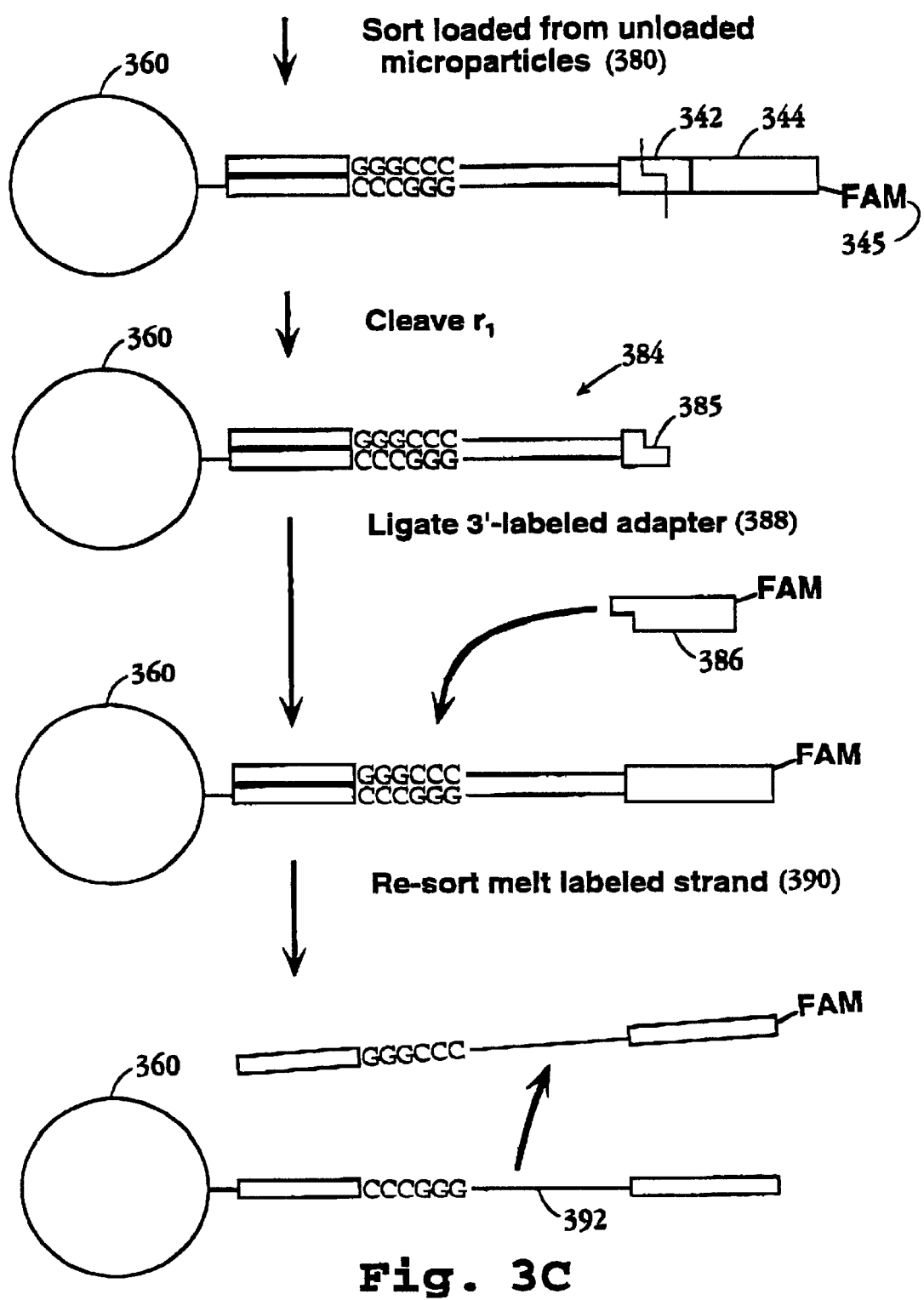
FIG. 3c illustrates a preferred scheme for isolating sorted cDNAs for cloning and sequencing.

As shown in FIG. 3c, after FACS, or like sorting (380), loaded microparticles (360) are isolated, treated to remove label (345), and treated to melt off the non-covalently attached strand. Label (345) is removed or inactivated so that it does not interfer with the labels of the competitively hybridized strands. Preferably, the tag-cDNA conjugates are treated with a restriction endonuclease recognizing site $r_1$ (342) which cleaves the tag-cDNA conjugates adjacent to primer binding site (344), thereby removing label (345) carried by the "bottom" strand, i.e. the strand have its 5' end distal to the microparticle. Preferably, this cleavage results in microparticle (360) with double stranded tag-cDNA conjugate (384) having protruding strand (385). 3'-labeled adaptor (386) is then annealed and ligated to protruding strand (385), after which the loaded microparticles are re-sorted by means of the 3'-label and the strand carrying the 3'-label is melted off to leave a covalently attached single strand of the cDNA (392) ready to accept denatured cDNAs or mRNAs from differentially expressed genes. Preferably, the 3'-labeled strand is melted off with sodium hydroxide treatment, or treatment with like reagent.

Oligonucleotide Tags for Identification and Solid Phase Cloning

An important feature of the invention is the use of oligonucleotide tags which are members of a minimally cross-hybridizing set of oligonucleotides to construct reference DNA populations attached to solid phase supports, preferably microparticles. The sequences of oligonucleotides of a minimally cross-hybridizing set differ from the sequences of every other member of the same set by at least two nucleotides. Thus, each member of such a set cannot form a duplex (or triplex) with the complement of any other member with less than two mismatches. Complements of oligonucleotide tags, referred to herein as "tag complements," may comprise natural nucleotides or non-natural nucleotide analogs. When oligonucleotide tags are used for sorting, as is the case for constructing a reference DNA population, tag complements are preferably attached to solid phase supports. Oligonucleotide tags when used with their corresponding tag complements provide a means of enhancing specificity of hybridization for sorting, tracking, or labeling molecules, especially polynucleotides, such as cDNAs or mRNAs derived from expressed genes.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross- hybridizing set may consist of a set of individually synthesized 10-mer sequences that differ from each other by at least 4 nucleotides, such set having a maximum size of 332, when constructed as disclosed in Brenner et al, International patent application PCT/US96/ 09513. Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers.

When synthesized combinatorially, an oligonucleotide tag preferably consists of a plurality of subunits, each subunit consisting of an oligonucleotide of 3 to 9 nucleotides in length wherein each subunit is selected from the same minimally cross-hybridizing set. In such embodiments, the number of oligonucleotide tags available depends on the number of subunits per tag and on the length of the subunits.

Complements of oligonucleotide tags attached to one or more solid phase supports are used to sort polynucleotides from a mixture of polynucleotides each containing a tag. Such tag complements are synthesized on the surface of a solid phase support, such as a microscopic bead or a specific location on an array of synthesis locations on a single support, such that populations of identical, or substantially identical, sequences are produced in specific regions. That is, the surface of each support, in the case of a bead, or of each region, in the case of an array, is derivatized by copies of only one type of tag complement having a particular sequence. The population of such beads or regions contains a repertoire of tag complements each with distinct sequences. As used herein in reference to oligonucleotide tags and tag complements, the term "repertoire" means the total number of different oligonucleotide tags or tag complements that are employed for solid phase cloning (sorting) or identification. A repertoire may consist of a set of minimally cross-hybridizing set of oligonucleotides that are individually synthesized, or it may consist of a concatenation of oligonucleotides each selected from the same set of minimally cross-hybridizing oligonucleotides. In the latter case, the repertoire is preferably synthesized combinatorially.

Preferably, tag complements are synthesized combinatorially on microparticles, so that each microparticle has attached many copies of the same tag complement. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from PE Applied Biosystems, Foster City, Calif.); derivatized magnetic beads; polystyrene grafted with polyethylene glycol (e.g., TentaGel™, Rapp Polymere, Tubingen Germany); and the like. Microparticles may also consist of dendrimeric structures, such as disclosed by Nilsen et al, U.S. Pat. No. 5,175,270. Generally, the size and shape of a microparticle is not critical; however, microparticles in the size range of a few, e.g. 1–2, to several hundred, e.g. 200–1000 µm diameter are preferable, as they facilitate the construction and manipulation of large repertoires of oligonucleotide tags with minimal reagent and sample usage. Preferably, glycidal methacrylate (GMA) beads available from Bangs Laboratories (Carmel, Ind.) are used as microparticles in the invention. Such microparticles are useful in a variety of sizes and are available with a variety of linkage groups for synthesizing tags and/or tag complements. More preferably, 5 μm diameter GMA beads are employed.

Polynucleotides to be sorted, or cloned onto a solid phase support, each have an oligonucleotide tag attached, such that different polynucleotides have different tags. This condition is achieved by employing a repertoire of tags substantially greater than the population of polynucleotides and by taking a sufficiently small sample of tagged polynucleotides from the full ensemble of tagged polynucleotides. After such sampling, when the populations of supports and polynucleotides are mixed under conditions which permit specific hybridization of the oligonucleotide tags with their respective complements, identical polynucleotides sort onto particular beads or regions. Of course, the sampled tag-polynucleotide conjugates are preferably amplified, e.g. by polymerase chain reaction, cloning in a plasmid, RNA transciption, or the like, to provide sufficient material for subsequent analysis.

Oligonucleotide tags are employed for two different purposes in certain embodiments of the invention: Oligonucleotide tags are employed to implement solid phase cloning, as described in Brenner, U.S. Pat. No. 5,604,097; and International patent application PCT/US96/09513, wherein large numbers of polynucleotides, e.g. several thousand to several hundred thousand, are sorted from a mixture into clonal subpopulations of identical polynucleotides on one or more solid phase supports for analysis, and they are employed to deliver (or accept) labels to identify polynucleotides, such as encoded adaptors, that number in the range of a few tens to a few thousand, e.g. as disclosed in Albrecht et al, International patent application PCT/US97/09472. For the former use, large numbers, or repertoires, of tags are typically required, and therefore synthesis of individual oligonucleotide tags is difficult. In these embodiments, combinatorial synthesis of the tags is preferred. On the other hand, where extremely large repertoires of tags are not required—such as for delivering labels to a plurality of kinds or subpopulations of polynucleotides in the range of 2 to a few tens, e.g. encoded adaptors, oligonucleotide tags of a minimally cross-hybridizing set may be separately synthesized, as well as synthesized combinatorially.

Sets containing several hundred to several thousands, or even several tens of thousands, of oligonucleotides may be synthesized directly by a variety of parallel synthesis approaches, e.g. as disclosed in Frank et al, U.S. Pat. No. 4,689,405; Frank et al, Nucleic Acids Research, 11: 4365–4377 (1983); Matson et al, Anal. Biochem., 224: 110–116 (1995); Fodor et al, International application PCT/US93/04145; Pease et al, Proc. Natl. Acad. Sci., 91: 5022–5026 (1994); Southern et al, J. Biotechnology, 35: 217–227 (1994), Brennan, International application PCT/US94/05896; Lashkari et al, Proc. Natl. Acad. Sci., 92: 7912–7915 (1995); or the like.

Preferably, tag complements in mixtures, whether synthesized combinatorially or individually, are selected to have similar duplex or triplex stabilities to one another so that perfectly matched hybrids have similar or substantially identical melting temperatures. This permits mismatched tag complements to be more readily distinguished from perfectly matched tag complements in the hybridization steps, e.g. by washing under stringent conditions. For combinatorially synthesized tag complements, minimally cross-hybridizing sets may be constructed from subunits that make approximately equivalent contributions to duplex stability as every other subunit in the set. Guidance for carrying out such selections is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Biol., 26: 227–259 (1991); and the like. A minimally cross-hybridizing set of oligonucleotides can be screened by additional criteria, such as GC-content, distribution of mismatches, theoretical melting temperature, and the like, to form a subset which is also a minimally cross-hybridizing set.

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

Oligonucleotide tags for sorting may range in length from 12 to 60 nucleotides or basepairs. Preferably, oligonucleotide tags range in length from 18 to 40 nucleotides or basepairs. More preferably, oligonucleotide tags range in length from 25 to 40 nucleotides or basepairs. In terms of preferred and more preferred numbers of subunits, these ranges may be expressed as follows:

| Numbers of Subunits in Tags in Preferred Embodiments | | | |
|---|---|---|---|
| Monomers | Nucleotides in Oligonucleotide Tag | | |
| in Subunit | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags for sorting are single stranded and specific hybridization occurs via Watson-Crick pairing with a tag complement.

Preferably, repertoires of single stranded oligonucleotide tags for sorting contain at least 100 members; more preferably, repertoires of such tags contain at least 1000 members; and most preferably, repertoires of such tags contain at least 10,000 members.

Preferably, the length of single stranded tag complements for delivering labels is between 8 and 20. More preferably, the length is between 9 and 15.

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrinidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments. Conditions for annealing single-stranded or duplex tags to their single-stranded or duplex complements are well known, e.g. Ji et al, Anal. Chem. 65: 1323–1328 (1993); Cantor et al, U.S. Pat. No. 5,482,836; and the like. Use of triplex tags in sorting has the advantage of not requiring a "stripping" reaction with polymerase to expose the tag for annealing to its complement.

An exemplary tag library for sorting is shown below (SEQ ID NO: 1).

If a sample of n tag-DNA sequence conjugates are randomly drawn from a reaction mixture—as could be effected by taking a sample volume, the probability of drawing conjugates having the same tag is described by the Poisson distribution, $P(r)=e^{-\lambda} (\lambda)^r/r$, where r is the number of conjugates having the same tag and $\lambda=np$, where p is the probability of a given tag being selected. If $n=10^6$ and $p=1/(1.67\times10^7)$ (for example, if eight 4-base words described in Brenner et al were employed as tags), then $\lambda=0.0149$ and $P(2)=1.13\times10^{-4}$. Thus, a sample of one million molecules gives rise to an expected number of doubles well within the preferred range. Such a sample is readily obtained by serial dilutions of a mixture containing tag-fragment conjugates.

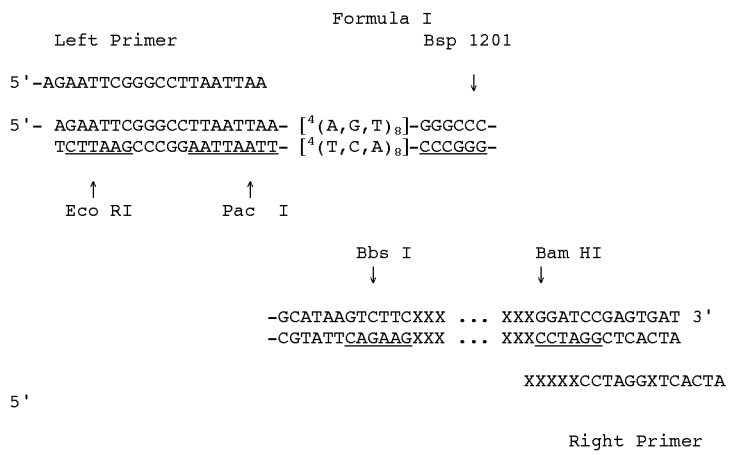

Formula I

The flanking regions of the oligonucleotide tag may be engineered to contain restriction sites, as exemplified above, for convenient insertion into and excision from cloning vectors. Optionally, the right or left primers may be synthesized with a biotin attached (using conventional reagents, e.g. available from Clontech Laboratories, Palo Alto, Calif.) to facilitate purification after amplification and/or cleavage. Preferably, for making tag-fragment conjugates, the above library is inserted into a conventional cloning vector, such a pUC19, or the like. Optionally, the vector containing the tag library may contain a "stuffer" region, "XXX . . . XXX," which facilitates isolation of fragments fullly digested with, for example, Bam HI and Bbs I.

An important aspect of the invention is the sorting and attachment of populations of DNA sequences, e.g. from a cDNA library, to microparticles or to separate regions on a solid phase support such that each microparticle or region has substantially only one kind of sequence attached; that is, such that the DNA sequences are present in clonal subpopulations. This objective is accomplished by insuring that substantially all different DNA sequences have different tags attached. This condition, in turn, is brought about by taking only a sample of the flll ensemble of tag-DNA sequence conjugates for analysis. (It is acceptable that identical DNA sequences have different tags, as it merely results in the same DNA sequence being operated on or analyzed twice.) Such sampling can be carried out either overtly—for example, by taking a small volume from a larger mixture—after the tags have been attached to the DNA sequences; it can be carred out inherently as a secondary effect of the techniques used to process the DNA sequences and tags; or sampling can be carried out both overtly and as an inherent part of processing steps.

As used herein, the term "substantially all" in reference to attaching tags to molecules, especially polynucleotides, is meant to reflect the statistical nature of the sampling procedure employed to obtain a population of tag-molecule conjugates essentially free of doubles. Preferably, at least ninety-five percent of the DNA sequences have unique tags attached.

Preferably, DNA sequences are conjugated to oligonucleotide tags by inserting the sequences into a conventional cloning vector carrying a tag library. For example, cDNAs may be constructed having a Bsp 120 I site at their 5' ends and after digestion with Bsp 120 I and another enzyme such as Sau 3A or Dpn II may be directionally inserted into a pUC19 carrying the tags of Formula I to form a tag-cDNA library, which includes every possible tag-cDNA pairing. A sample is taken from this library for amplification and sorting. Sampling may be accomplished by serial dilutions of the library, or by simply picking plasmid-containing bacterial hosts from colonies. After amplification, the tag-cDNA conjugates may be excised from the plasmid.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26: 227–259 (1991); Sambrook et al, Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

Specificity of the hybridizations of tag to their complements may be increased by taking a sufficiently small sample so that both a high percentage of tags in the sample are unique and the nearest neighbors of substantially all the tags in a sample differ by at least two words. This latter condition may be met by taking a sample that contains a number of tag-polynucleotide conjugates that is about 0.1 percent or less of the size of the repertoire being employed. For example, if tags are constructed with eight words a repertoire of $8^8$, or about $1.67 \times 10^7$, tags and tag complements are produced. In a library of tag-DNA sequence conjugates as described above, a 0.1 percent sample means that about 16,700 different tags are present. If this were loaded directly onto a repertoire-equivalent of microparticles, or in this example a sample of $1.67 \times 10^7$ microparticles, then only a sparse subset of the sampled microparticles would be loaded. Preferably, loaded microparticles may be separated from unloaded microparticles by a fluorescence activated cell sorting (FACS) instrument using conventional protocols after DNA sequences have been fluorescently labeled and denatured. After loading and FACS sorting, the label may be cleaved prior use or other analysis of the attached DNA sequences.

A reference DNA population may consist of any set of DNA sequences whose frequencies in different test populations is sought to be compared. Preferably, a reference DNA population for use in the analysis of gene expression in a plurality of cells or tissues is constructed by generating a cDNA library from each of the cells or tissues whose gene expression is being compared. This may be accomplished either by pooling the mRNA extracted from the various cells and/or tissues, or it may be accomplished by pooling the cDNAs of separately constructed cDNA libraries. The objective is to obtain a set of DNA sequences that will include all of the sequences that could possibly be expressed in any of the cells or tissues being analyzed. Once the DNA sequences making up a reference DNA population are obtained, they must be conjugated with oligonucleotide tags for solid phase cloning. Preferably, the DNA sequences are prepared so that they can be inserted into a vector carrying an appropriate tag repertoire, as described above, to form a library of tag-DNA sequence conjugates. A sample of conjugates is taken from this library, amplified, and loaded onto microparticles. It is important that the sample be large enough so that there is a high probability that all of the different types of DNA sequences are represented on the loaded microparticles. For example, if among a plurality of cells being compared a total of about 25,000 genes are expressed, then a sample of about five-fold this number, or about 125,000 tag-DNA sequence conjugates, should be taken to ensure that all possible DNA sequences will be represented among the loaded microparticles with about a 99% probability, e.g. Sambrook et al (cited above).

Preferably, after the tag-DNA sequence conjugates are sampled, they are amplified by PCR using a fluorescently labeled primer to provide sufficient material to load onto the tag complements of the microparticles and to provide a means for distinguishing loaded from unloaded microparticles, as disclosed in Brenner et al (cited above). Preferably, the PCR primer also contains a sequence which allows the generation of a restriction site of a rare-cutting restriction endonuclease, such as Pac I, in the double stranded product so that the fluorescent label may be cleave from the end of the cDNA prior to the competitive hybridization of labeled DNA strands derived from cells or tissue being studied. After such loading, the specifically hybridized tag-DNA sequence conjugates are ligated to the tag complements and the loaded microparticles are separated from the unloaded microparticles by FACS. The fluorescent label is cleaved from the DNA strands of the loaded microparticles and the non-covalently attached strand is removed by denaturing with heat, formamide, NaOH, and/or with like means, using conventional protocols. The microparticles are then ready for competitive hybridization.

Competitive Hybridization and Ligt-Generating Labels

Gene expression products, e.g. M/RNA or cDNA, from the cells and/or tissues being analyzed are isolated and labeled by conventional techniques, e.g. DeRisi et al (cited above), or the like. Preferably, a light-generating label is incorporated into cDNAs reverse transcribed from the extracted M/RNA, or an oligonucleotide tag is attached for providing a labeled tag complement for identification. A large number of light-generating labels are available, including fluorescent, calorimetric, chemiluminescent, and electroluminescent labels. Generally, such labels produce an optical signal which may comprise an absorption frequency, an emission frequency, an intensity, a signal lifetime, or a combination of such characteristics. Preferably, fluorescent labels are employed, either by direct incorporation of fluorescently labeled nucleoside triphosphates or by indirect application by incorporation of a capture moiety, such as biotinylated nucleoside triphosphates or an oligonucleotide tag, followed by complexing with a moiety capable of generating a fluorescent signal, such as a streptavidin-fluorescent dye conjugate or a fluorescently labeled tag complement. Preferably, the optical signal detected from a fluorescent label is an intensity at one or more characteristic emission frequencies. Selection of fluorescent dyes and means for attaching or incorporating them into DNA strands is well known, e.g. DeRisi et al (cited above), Matthews et al, Anal. Biochem., Vol 169, pgs. 1–25 (1988); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227–259 (1991); Ju et al, Proc. Natl. Acad. Sci., 92: 4347–4351 (1995) and Ju et al, Nature Medicine, 2: 246–249 (1996); and the like.

Preferably, light-generating labels are selected so that their respective optical signals can be related to the quantity of labeled DNA strands present and so that the optical signals generated by different light-generating labels can be compared. Measurement of the emission intensities of fluorescent labels is the preferred means of meeting this design objective. For a given selection of fluorescent dyes, relating their emission intensities to the respective quantities of labeled DNA strands requires consideration of several factors, including fluorescent emission maxima of the different dyes, quantum yields, emission bandwidths, absorption maxima, absorption bandwidths, nature of excitation light source(s), and the like. Guidance for making fluorescent intensity measurements and for relating them to quantities of analytes is available in the literature relating to chemical and molecular analysis, e.g. Guilbault, editor, Practical Fluorescence, Second Edition (Marcel Dekker, New York, 1990); Pesce et al, editors, Fluorescence Spectroscopy (Marcel Dekker, New York, 1971); White et al, Fluorescence Analysis: A Practical Approach (Marcel Dekker, New York, 1970); and the like. As used herein, the term "relative optical signal" means a ratio of signals from different light-generating labels that can be related to a ratio of differentlly labeled DNA strands of identical, or substantially identical, sequence that form duplexes with a complementary reference DNA strand. Preferably, a relative optical signal is a ratio of fluorescence intensities of two or more different fluorescent dyes.

Competitive hybridization between the labeled DNA strands derived from the plurality of cells or tissues is carried out by applying equal quantities of the labeled DNA strands from each such source to the microparticles loaded with the reference DNA population in a conventional hybridization reaction. The particular amounts of labeled DNA strands added to the competitive hybridization reaction vary widely depending on the embodiment of the invention. Factors influencing the selection of such amounts include the quantity of microparticles used, the type of microparticles used, the loading of reference DNA strands on the microparticles, the complexity of the populations of labeled DNA strands, and the like. Hybridization is competitive in that differently labeled DNA strands with identical, or substantially identical, sequences compete to hybridize to the same complementary reference DNA strands. The competitive hybridization conditions are selected so that the proportion of labeled DNA strands forming duplexes with complementary reference DNA strands reflects, and preferably is directly proportional to, the amount of that DNA strand in its population in comparison with the amount of the competing DNA strands of identical sequence in their respective populations. Thus, if a first and second differently labeled DNA strands with identical sequence are competing for hybridization with a complementary reference DNA strand such that the first labeled DNA strand is at a concentration of 1 ng/$\mu$l and the second labeled DNA strand is at a concentration of 2 ng/$\mu$l, then at equilibrium it is expected that one third of the duplexes formed with the reference DNA would include first labeled DNA strands and two thirds of the duplexes would include second labeled DNA strands. Guidance for selecting hybridization conditions is provided in many references, including Keller and Manak, (cited above); Wetmur, (cited above); Hames et al, editors, Nucleic Acid Hybridization: A Practical Approach (IRL Press, Oxford, 1985); and the like.

Figure 1B:
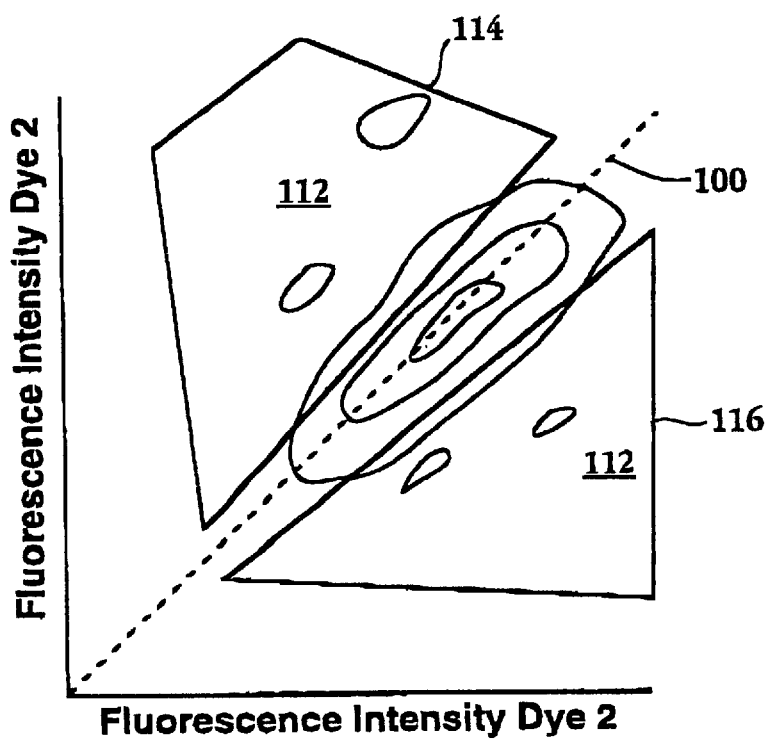

Flow Sorting of Microparticles with Up-Regulated and/or Down-Regulated Gene Products Microparticles containing fluorescently labeled DNA strands are conveniently classified and sorted by a commercially available FACS instrument, e.g. Van Dilla et al, Flow Cytometry: Instrumentation and Data Analysis (Academic Press, New York, 1985). For fluorescently labeled DNA strands competitively hybridized to a reference strand, preferably the FACS instrument has multiple fluorescent channel capabilities. Preferably, upon excitation with one or more high intensity light sources, such as a laser, a mercury arc lamp, or the like, each microparticle will generate fluorescent signals, usually fluorescence intensities, related to the quantity of labeled DNA strands from each cell or tissue types carried by the microparticle. As shown in FIG. 1a of Example 1, when fluorescent intensities of each microparticle are plotted on a two-dimensional graph, microparticles indicating equal expression levels will be on or near the diagonal (100) of the graph. Up-regulated and down-regulated genes will appear in the off-diagonal regions (112). Such microparticles are readily sorted by commercial FACS instruments by graphically defining sorting parameters to enclose one or both off-diagonal regions (112) as shown in FIG. 1b.

Identification of Sorted Genes by Massively Parallel Signature Sequencing (MPSS)

Expressed genes may be identified in parallel by MPSS, which is a combination of two techniques: one for tagging and sorting fragments of DNA for parallel processing (e.g. Brenner et al, International application PCT/US96/09513), and another for the stepwise sequencing the end of a DNA fragment (e.g. Brenner, U.S. Pat. No. 5,599,675 and Albrecht et al, International patent application PCT/US97/09472). After an initial digestion of a target polynucleotide with a first restriction endonuclease, restriction fragments are ligated to oligonucleotide tags as described below, and in Brenner et al, International application PCT/US96/09513, so that the resulting tag-fragment conjugates may be sampled, amplified, and sorted onto separate solid phase supports by specific hybridization of the oligonucleotide tags with their tag complements.

Once an amplified sample of DNA fragments is sorted onto solid phase supports to form homogeneous populations of substantially identical fragments, the ends of the fragments are preferably sequenced with an adaptor-based method of DNA sequencing that includes repeated cycles of ligation, identification, and cleavage, such as the method described in Brenner, U.S. Pat. No. 5,599,675. In further preference, adaptors used in the sequencing method each have a protruding strand and an oligonucleotide tag selected from a minimally cross-hybridizing set of oligonucleotides, as taught by Albrecht et al, International patent application PCT/US97/09472. Such adaptors are referred to herein as "encoded adaptors." Encoded adaptors whose protruding strands form perfectly matched duplexes with the complementary protruding strands of a fragment are ligated. After ligation, the identity and ordering of the nucleotides in the protruding strand is determined, or "decoded," by specifically hybridizing a labeled tag complement, or "de-coder" to its corresponding tag on the ligated adaptor.

The preferred sequencing method is carried out with the following steps: (a) ligating an encoded adaptor to an end of a fragment, the encoded adaptor having a nuclease recognition site of a nuclease whose cleavage site is separate from its recognition site; (b) identifying one or more nucleotides at the end of the fragment by the identity of the encoded adaptor ligated thereto; (c) cleaving the fragment with a nuclease recognizing the nuclease recognition site of the encoded adaptor such that the fragment is shortened by one or more nucleotides; and (d) repeating said steps (a) through (c) until said nucleotide sequence of the end of the fragment is determined. In the identification step, successive sets of tag complements, or "de-coders," are specifically hybridized to the respective tags carried by encoded adaptors ligated to the ends of the fragments. The type and sequence of nucleotides in the protruding strands of the polynucleotides are identified by the label carried by the specifically hybridized de-coder and the set from which the de-coder came, as described below.

Identification of Sorted Genes by Conventional Sequencing

Figure 4A:
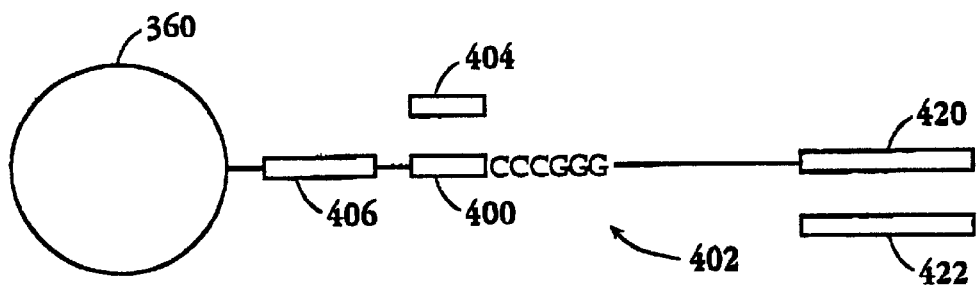
FIGS. 4a and 4b illustrate alternative procedures for cloning differentially expressed cDNAs isolated by FACS sorting.

Gene products carried by microparticles may be identified after sorting, e.g. by FACS, using conventional DNA sequencing protocols. Suitable templates for such sequencing may be generated in several different ways starting from the sorted microparticles carrying differentially expressed gene products. For example, the reference DNA attached to an isolated microparticle may be used to generate labeled extension products by cycle sequencing, e.g. as taught by Brenner, International application PCT/US95/12678. In this embodiment, primer binding site (400) is engineered into the reference DNA (402) distal to tag complement (406), as shown in FIG. 4a. After isolating a microparticle, e.g. by sorting into separate microtiter well, or the like, the differentially expressed strands are melted off, primer (404) is added, and a conventional Sanger sequencing reaction is carried out so that labeled extension products are formed. These products are then separated by electrophoresis, or like techniques, for sequence determination. In a similar embodiment, sequencing templates may be produced without sorting individual microparticles. Primer binding sites (400) and (420) may be used to generate templates by PCR using primers (404) and (422). The resulting amplicons containing the templates are then cloned into a conventional sequencing vector, such as M13. After transfection, hosts are plated and individual clones are selected for sequencing.

Figure 4B:
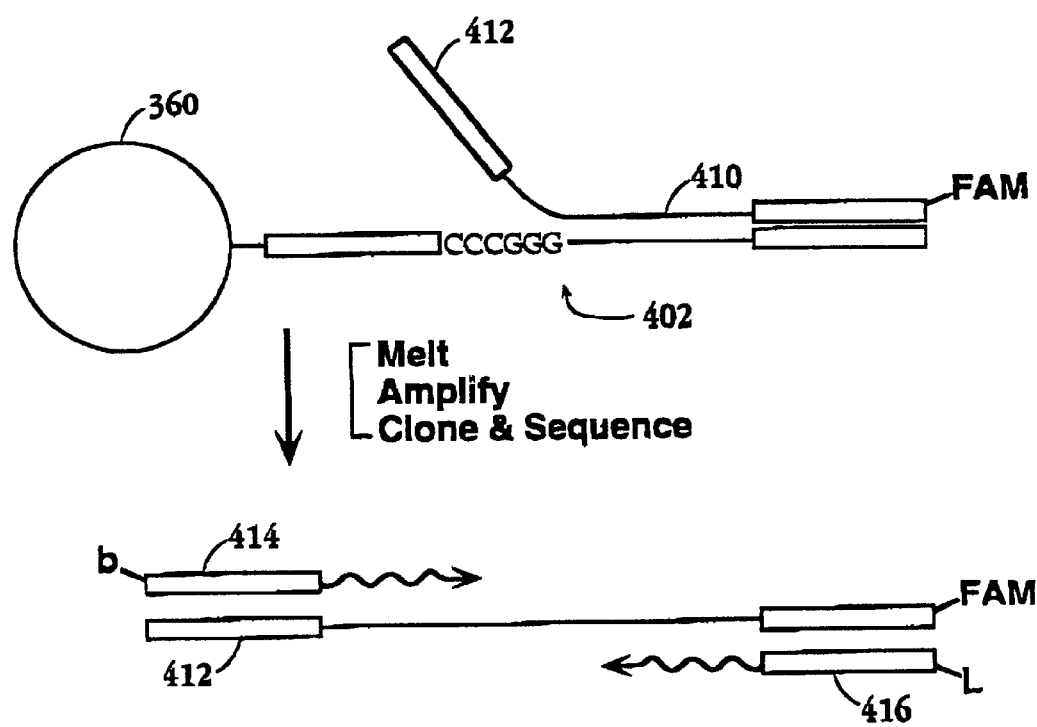

In another embodiment, illustrated in FIG. 4b, primer binding site (412) may be engineered into the competitively hybridized strands (410). This site need not have a complementary strand in the reference DNA (402). After sorting, competitively hybridized strands (410) are melted off of reference DNA (402) and amplified, e.g. by PCR, using primers (414) and (416), which may be labeled and/or derivatized with biotin for easier manipulation. The melted and amplified strands are then cloned into a conventional sequencing vector, such as M13, which is used to transfect a host which, in turn, is plated. Individual colonies are picked for sequencing.

EXAMPLE 1

Construction of a Tagged cDNA Library Sampling, and Loading Tagged cDNAs onto Microparticles In this example, a preferred protocol for preparing tagged reference DNA for loading onto microparticles is described.

conjugates are preferably amplified from the vectors by PCR and processed as described below for loading onto microparticles derivatized with tag complements. After the non-covalently attached strand is melted off, the cDNA-containing microparticles are ready to accept competitively hybridized gene products in accordance with the invention. Specific guidance relating to the indicated steps is available in Sambrook et al (cited above); Ausbel et al, editors, Current Protocols in Molecular Biology (John Wiley & Sons, New York, 1995); and like guides on molecular biology techniques.

A pellet of approximately 5 μg of mRNA is resuspended in 45 μl (final volume) of a first strand pre-mix consisting of 10 μl 5× SuperScript buffer (250 mM Tris-Cl, pH 8.3, 375 mM KCl, and 15 mM $MgCl_2$) (GIBCO/BRL) (or like reverse transcriptase buffer), 5 μl 0.1 M dithiothreitol (DTT), 2.5 μl 3dNTP/methyl-dCTP mix (10 μM each of dATP, dGTP, dTTP, and 5-methyl-dCTP, e.g available from Pharmacia Biotech), 1 μl RNasin, 12 μl 0.25 μg/μl of reverse transcription primer shown below, and 14.5 μl $H_2O$.

5'-biotin-GACATGC CTY CATTGAGACGAT-TCTTTTTTTTTTTTTTTV

Reverse Transcription Primer (SEQ ID NO: 2)

After incubation for 15 min at room temperature, 5 ml of 200 U/μl SuperScript is added and the mixture is incubated for 1 hr at 42° C. After the 1 hr incubation, the above mixture (about 50 μl total) is added to a second-strand premix on ice (volume 336 ∥l) consisting of 80 μl 5× second-strand buffer (94 mM Tris-Cl, pH 6.9, 453 mM KCl, 23 MM $MgCl_2$, and 50 mM $(NH_4)2SO_4$ to give a total reaction volume of about 386 μl. Separately, 4 μl of 0.8 U/μl RNase H (3.2 units) and 10 μl of 10 unit/μl E. coli DNA polymerase I (100 units) are combined and the combined enzyme mixture is added to the above second-strand reaction mixture, after which the total reaction volume is microfuged 5 sec and then incubated for 1 hr at 16° C. and for 1 hr at room temperature to give the following double stranded cDNA (SEQ ID NO: 3):

```
5'-biotin-GACATGCTGCATTGAGACGATTCTTTTTTTTTTTTTTTTVXXX ... XGATCXXX-3'
          CTGTACGACGTAACTCTGCTAAGAAAAAAAAAAAAAAAAAABXXX ... XCTAGXXX-5'
                      ↑                                    ↑         t
                    Bsm BI                               Dpn II
```

Briefly, cDNA from each of the cell or tissue types of interest is prepared and directionally cloned into a vector containing the tag element of Formula I. Preferably, the M/RNA extracted from such cells or tissues is combined, usually in equal proportions, prior to first strand synthesis. M/RNA is obtained using standard protocols, after which first and second strand synthesis is carried out as exemplified and the resulting cDNAs are inserted into a vector containing a tag element of Formula I, or like tag element. The vectors containing the tag-cDNA conjugates are then used to transform a suitable host, typically a conventional bacterial host, after which a sample of cells from the host culture is further expanded and vector DNA is extracted. The tag-cDNA where the X's indicated nucleotides in the cDNAs, V represents A, C, or G, and B represents C, G, or T. Note that the reverse transcription primer sequence has been selected to give a Bsm BI site in the cDNAs which results in a 5'-GCAT overhang upon digestion with Bsm BI.

After phenol/chloroform extraction and ethanol precipitation, the cDNA is resuspended in the manufacturer's recommended buffer for digestion with Dpn II (New England Biolabs, Beverely, Mass.), which is followed by capture of the biotinylated fragment on avidinated beads (Dynal, Oslo, Norway). After washing, the captured fragments are digested with Bsm BI to release the following cDNAs (SEQ ID NO: 4) which are precipitated in ethanol:

```
GCATTGAGACGATTCTTTTTTTTTTTTTTTTVXXX ... X      -3'
ACTCTGCTAAGAAAAAAAAAAAAAAAAAABXXX ... XCTAG -5'
```

A conventional cloning vector, such as BlueScript II, pBC, or the like (Stratagene Cloning Systems, La Jolla, Calif.), is engineered to have the following sequence of elements (SEQ ID NO: 5)(which are those shown in Formula I):

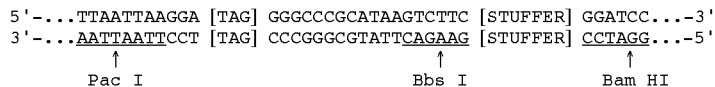

After digestion with Bbs I and Bam HI, the vector is purified by gel electrophoresis and combined with the cDNAs for ligation. Note that the vector has been engineered so that the Bbs I digestion results in an end compatible with the Bsm BI-digested end of the cDNAs. After ligation, a suitable host bacteria is transformed and a culture is expanded for subsequent use.

From the expanded culture, a sample of host cells are plated to determine the fraction that carry vectors with inserted cDNAs, after which an aliquot of culture corresponding to about $1.7 \times 10^5$ insert-containing cells is withdrawn and separately expanded in culture. This represents about one percent of the repertoire of tags of the type illustrated in Formula I.

Preferably, the tag-cDNA conjugates are amplified out of the vectors by PCR using a conventional protocol, such as the following. For each of 8 replicate PCRs, the following reaction components are combined: 1 µl vector DNA (125 ng/µl for a library, $10^9$ copies for a single clone); 10 µl 10× Klentaq Buffer (Clontech Laboratories, Palo Alto, Calif.); 0.25 µl biotinylated 20-mer "forward" PCR primer (1 nmol/µl); 0.25 µl FAM-labeled 20-mer "reverse" PCR primer (1 nmol/µl); 1 µl 25 mM dATP, dGTP, dTTP, and 5-methyl-dCTP (total dNTP concentration 100 mM); 5 µl DMSO; 2 µl 50× Klentaq enzye; and 80.5 µl H₂0 (for a total volume of 100 µl). The PCR is run in an MJR DNA Engine (MJ Research), or like thermal cycler, with the following protocol: 1) 94° C. for 4 min; 2) 94° C. 30 sec; 3) 67° C. 3 min; 4) 8 cycles of steps 2 and 3; 5) 94° C. 30 sec, 6) 64° C. 3 min, 7) 22 cycles of steps 5 and 6; 8) 67° C. for 3 min; and 9) hold at 40C.

The cleaved DNA is extracted with phenol/chloroform followed by ethanol precipitation. The tags of the tag-cDNA conjugates are rendered single stranded by combining 2 units of T4 DNA polymerase (New England Biolabs) per fg of streptavidin-purified DNA. 150 µg of streptavidin-purified DNA is resuspended in 200 µl H₂O and combined with the following reaction components: 30 µl 10 NEB Buffer No. 2 (New England Biolabs); 9 µl 100 mM dGTP; 30 µl T4 DNA polymerase (10 units/µl); and 31 µl H₂O; to give a final reaction volume of 300 µl. After incubation for 1 hr at 37° C., the reaction is stopped by adding 20 µl 0.5 M EDTA, and the T4 DNA polymerase is inactivated by incubating the reaction mixture for 20 min at 75° C. The tag-cDNA conjugates are puified by phenol/chloroform extraction and ethanol precipitation.

5 µm GMA beads with tag complements are prepared by combinatorial synthesis on an automated DNA synthesizer (Gene Assembler Special /4 Primers, Pharmacia Biotech, Bjorkgatan, Sweden, or like instument) using conventional phosphoramidite chemistry, wherein nucleotides are condenced in the 3'→5' direction. In a preferred embodiment, a 28-nucleotide "spacer" sequence is synthesized, followed by the tag complement sequence (8 "words" of 4 nucleotides each for a total of 32 nucleotides in the tag complement), and a sequence of three C's. Thus, the beads are devivatized with a 63-mer oligonucleotide. The length of the "spacer" sequence is not critical; however, the proximity of the bead surface may affect the activity of enzymes that are use to treat tag complements or captured sequences. Therefore, if such processing is employed, a spacer long enough to avoid such surface effects is desirable. Preferably, the spacer is between 10 and 30 nucleotides, inclusive. The following sequence (SEQ ID NO: 6), containing a Pac I site, is employed in the present embodiment:

The 8 PCR mixtures are pooled and 700 µlphenol is added at room temperature, after which the combined mixture is vortexed for 20–30 sec and then centrifuged at high speed (e.g. 14,000 rpm in an Eppendorf bench top centrifuge, or like instrument) for 3 min. The supernatant is removed and combined with 700 µl chloroform (24:1 mixture of chloroform:iso-amyl alcohol) in a new tube, vortexed for 20–30 sec, and centrifuged for 1 min, after which the supernatant is transferred to a new tube and combined with 80 µl 3M sodium acetate and 580 µl isopropanol. After centrifuging for 20 min, the supernatant is removed and 1 ml 70% ethanol is added. The mixture is centrifuged for 5–10 min, after which the ethanol is removed and the precipitated DNA is dried in a speedvac.

After resuspension, the cDNA is purified on avidinated magnetic beads (Dynal) using the manufacturer's recommended protocol and digested with Pac I (1 unit of enzyme per µg of DNA), also using the manufacturer's recommended protocol (New England Biolabs, Beverly, Mass.)

Preferably, the tag-cDNA conjugates are hybridized to tag compliments on beads of a number corresponding to at least a full repertoire of tag complements, which in the case of the present embodiment is $8^8$, or about $1.6 \times 10^7$ beads. The number of beads in a given volume is readily estimated with a hemocytometer.

Prior to hybridization of the tag-cDNA conjugates, the 5' ends of the tag complements are phosphorylated, preferably by treatment with a polynucleotide kinase. Briefly, $2.5 \times 10^8$ beads suspended in 100 µl H₂O are combined with 100 µl 10× NEB buffer No. 2 (New England Biolabs, Beverly, Mass.), 10µl 100 mM ATP, 1 µl 10% Tween 20, 17 µl T4 polynucleotide kinase (10 units/µl), and 772 µl H₂O for a final volume of 1000 µl. After incubating for 2 hr at 37° C. with vortexing, the temperature is increased to 65° C. for 20 min to inactivate the kinase, with continued vortexing. After incubation, the beads are washed twice by spinning down the beads and resuspending them in 1 ml TE (Sambrook et al, Molecular Cloning, Second Edition, Cold Spring Harbor Laboratory) containing 0.01% Tween 20.

For hybridization of tag-cDNA conjugates to tag complements, the tag-cDNA conjugates as prepared above are suspended in 50 µl H₂O and the resulting mixture is combined with 40 µl 2.5× hybridization buffer, after which the combined mixture is filtered through a Spin-X spin column (0.22 µm) using a conventional protocol to give a filtrate containing the tag-cDNA conjugates. (5 ml of the 2.5× hybridization buffer consists of 1.25 ml 0.1 M NaPO₄ (pH 7.2), 1.25 ml 5 M NaCl, 0.25 ml 0.5% Tween 20, 1.50 ml 25% dextran sulfate, and 0.75 ml H₂O.) Appoximately 1.8×10⁷ beads in 10 µl TE/Tween buffer (TE with 0.01% Tween 20) is centrifuged so that the beads form a pellet and the TE/Tween is removed. To the beads, 25 µl of 1× hybridization buffer (10 mM NaPO₄ (pH 7.2), 500 mM NaCl, 0.01% Tween 20, 3% dextran sulfate) is added and the mixture is vortexed to fully resuspend the beads, after which the mixture is centrifuged so that the beads form a pellet and the supernatant is removed.

The tag-cDNA conjugates in the above filtrate are incubated at 75° C. for 3 min and combined with the beads, after which the mixture is vortexed to fully resuspend the beads. The resulting mixture is fuirther incubated at 75° C. with vortexing for approximately three days (60 hours). After hybridization, the mixture is centrifuged for 2 min and the supernatant is removed, after which the beads are washed twice with 500 µil TE/Tween and resuspended in 500 µl 1× NEB buffer No. 2 with 0.01% Tween 20. The beads are incubated at 64°C. in this solution for 30 min., after which the mixture is centrifuged so that the beads form a pellet, the supernatant is removed, and the beads are resuspended in 500 µl TE/Tween.

Loaded beads are sorted from unloaded beads using a high speed cell sorter, preferably a MoFlo flow cytometer equiped with an argon ion laser operating at 488 nm (Cytomation, Inc., Ft. Collins, Colo.), or like instrument. After sorting, the loaded beads are subjected to a fill-in reaction by combining them with the following reaction components: 10 µl 10×NEB buffer No. 2, 0.4 µl 25 mM dNTPs, 1 µl 1% Tween 20, 2 µl T4 DNA polymerase (10 units/ml), and 86.6 µl H₂O, for a final reaction volume of 100 µl. After incubation at 12° C. for 30 min with vortexing, the reaction mixture is centrifuged so that the beads form a pellet and the supernatant is removed. The pelleted beads are resuspended in a ligation buffer consisting of 15 µl 10×NEB buffer No. 2, 1.5 µl 1% Tween 20, 1.5 µl 100 mM ATP, 1 µl T4 DNA ligase (400 units/ ml), and 131 µl H₂O, to give a final volume of 150 µl. The ligation reaction mixture is incubated at 37° C. for 1 hr with vortexing, after which the beads are pelleted and washed once with 1× phosphate buffered saline (PBS) with 1 mM CaCl₂. The beads are resuspended in 45 µl PBS (with 1 mM CaCl₂) and combined with 6 µl Pronase solution (10 mg/ml, Boehringer Mannheim, Indianapolis, Ind.), after which the mixture is incubated at 37° C. for 1 hr with vortexing. After centrifugation, the loaded beads are washed twice with TE/Tween and then once with 1×NEB Dpn II buffer (New England Biolabs, Beverly, Mass.).

The tag-cDNA conjugates loaded onto beads are cleaved with Dpn II to produce a four-nucleotide protruding strand to which a complementary adaptor carying a 3'-label is ligated. Accordingly, the loaded beads are added to a reaction mixture consisting of the following components: 10 µl 10×NEB Dpn II buffer, 1 µl 1% Tween, 4 µl Dpn II (50 units/ml), and 85 µl H₂O, to give a final reaction volume of 100 µl. The mixture is incubated at 37° C. overnight with vortexing, after which the beads are pelleted, the supernatant is removed, and the beads are washed once with 1×NEB buffer No. 3. To prevent self-ligation, the protruding strands of the tag-cDNA conjugates are treated with a phosphatase, e.g. calf intestine phosphatase (CIP), to remove the 5' phosphates. Accordingly, the loaded beads are added to a reaction mixture consisting of the following components: 10 µl 10× NEB buffer No. 3, 1 µl 1% Tween 20, 5 µl CIP (10 units/µl), and 84 µl H₂O, to give a final reaction volume of 100 µl. The resulting mixture is incubated at 37° C. for 1 hr with vortexing, after which the beads are pelleted, washed once in PBS containing 1 mM CaCl₂, treated with Pronase as described above, washed twice with TE/Tween, and once with 1× NEB buffer No. 2.

The following 3'-labeled adaptor (SEQ ID NO: 7) is prepared using conventional reagents, e.g. Clontech Laboratories (Palo Alto, Calif.):

```
5'-pGATCACGAGCTGCCAGTC-FAM
    TGCTCGACGGTCAG
``` where "p" is a 5' phosphate group and "FAM" is a fluorescein dye attached to the 3' carbon of the last nucleotide of the top strand by a commercially available 3' linker group (Clontech Laboratories). The ligation is carried out in the following reaction mixture: 5 µl 10× NEB buffer No. 2, 0.5 µl 1% Tween 20, 0.5 µl 100 mM ATP, 5 ml 3'-labeled adaptor (100 pmol/µl), 2.5 µl T4 DNA ligase (400 units/A) and 36.5 µl H₂O, to give a final reaction volume of 50 µl. The reaction mixture is incubated at 16° C. overnight with vortexing, after which the beads are washed once with PBS containing 1 mM CaC₂ and treated with Pronase as described above. After this initial ligation, the nick remaining between the adaptor and tag-cDNA conjugate is sealed by simultaneously treating with both a kinase and a ligase as follows. Loaded beads are resuspended in a reaction mixture consisting of the following components: 15 µl 10× NEB buffer No. 2, 1.5 µl 1% Tween 20, 1.5 µl 100 mM ATP, 2 µl T4 polynucleotide kinase (10 units/µl), 1 µl T4 DNA ligase (400 units/µl), and 129 µl H₂O, for a final reaction volume of 150 µl. The reaction mixture is incubated at 37° C. for 1 hr with vortexing, after which the beads are washed once with PBS containing 1 mM CaCl₂, treated with Pronase as described above, and washed twice with TE/Tween.

After the labeled strand is melted off, preferably by treatment with 150 mM NaOH, the reference DNA on the beads is ready for competitive hybridization of differentially expressed gene products.

EXAMPLE 2

Preparation of a Yeast Reference DNA Population Attached to Microparticles

In this example, Saccharomyces cerevisiae cells of strain YJM920 MATa Gal+SUC2 CUP1 are grown in separate rich and minimal media cultures essentially as describe by Wodicka et al (cited above). mRNA extracted from cells grown under both conditions are used to establish a reference cDNA population which is tagged, sampled, amplified, labeled, and loaded onto microparticles. Loaded microparticles are isolated by FACS, labels are removed, and the non-covalently bound strands of the loaded DNA are melted off and removed.

Yeast cells are grown at 30° C. either in rich medium consisting of YPD (yeast extract/peptone/glucose, Bufferad, Newark, NJ) or in minimal medium (yeast nitrogen base without amino acids, plus glucose, Bufferad). Celldensity is measured by counting cells from duplicate dilutions, and the number of viable cells per milliliter is estimated by plating dilutions of the cultures on YPD agar immediately before collecting cells for MRNA extraction. Cells is mid-log phase (1–5×10⁷ cells/ml) are pelleted, washed twice with AE buffer solution (50 mM NaAc, pH 5.2, 10 mM EDTA), frozen in a dry ice-ethanol bath, and stored at −80° C.

mRNA is extracted as follows for both the construction of the reference DNA library and for preparation of DNA for competitive hybridization. Total RNA is extracted from frozen cell pellets using a hot phenol method, described by Schmitt et al, Nucleic Acids Research, 18: 3091–3092 (1990), with the addition of a chloroform-isoamyl alcohol extraction just befor precipitation of the total RNA. Phase-Lock Gel (5 Prime-3 Prime, Inc., Boulder, Colo.) is used for all organic extractions to increase RNA recovery and decrease the potential for contamination of the RNA with material from the organic interface. Poly(A)⁺ RNA is purified from the total RNA with an oligo-dT selection step (Oligotex, Qiagen, Chatsworth, Calif.).

5 $\mu$l each of mRNA from cells grown on rich medium and minimal medium are mixed for construction of a cDNA library in a pUC19 containing the tag repertoire of Formula I. The tag repertoire of Formula I is digested with Eco RI and Bam HI and inserted into a similarly digested pUC 19. The niRNA is reverse transcribed with a commercially available kit (Strategene, La Jolla, Calif.) using an olgio-dT primer containing a sequence which generates a Bsm BI site identical to that of Formula I upon second strand synthesis. The resulting cDNAs are cleaved with Bsm BI and Dpn II and inserted into the tag-containing pUC19 after digestion with Bsm BI and Bamr HI. After transfection and colony formation, the density of pUC 19 tranformants is determined so that a sample containing approximately thirty thousand tag-cDNA conjugates may be obtained and expanded in culture. Alternatively, a sample of tag-cDNA conjugates are obtained by picking approximately 30 thousand clones, which are then mixed and expanded in culture.

From a standard miniprep of plasmid, the tag-cDNA conjugates are amplified by PCR with 5-methyldeoxycytosine triphosphate substituted for deoxy-cytosine triphosphate. The following 19-mer forward and reverse primers (SEQ ID NO: 8 and SEQ ID NO: 9), specific for flanking sequences in pUC 19, are used in the reaction: forward primer: 5'-biotin-AGTGAATTCGGGCCTTAATTAA reverse primer: 5'-FAM-GTACCCGCGGCCGCGGTCGACTCTAGAGGATC where "FAM" is an NHS ester of fluorescein (Clontech Laboratories, Palo Alto, Calif.) coupled to the 5' end of the reverse primer via an amino linkage, e.g. Aminolinker 11 (Perkin-Elmer, Applied Biosystems Division, Foster City, Calif.). The reverse primer is selected so that a Not I site is reconstituted in the double stranded product. After PCR amplification, the tag-cDNA conjugates are isolated on avidinated beads, e.g. M-280 Dynabeads (Dynal, Oslo, Norway).

After washing, the cDNAs bound to the beads are digested with Pac I releasing the tag-cDNA conjugates and a stripping reaction is carried out to render the oligonucle-otide tags single stranded. After the reaction is quenched, the tag-cDNA conjugate is purified by phenol-chloroform extraction and combined with 5.5 $\mu$m GMA beads carrying tag complements, each tag complement having a 5' phosphate. Hybridization is conducted under stringent conditions in the presence of a thermal stable ligase so that only tags forming perfectly matched duplexes with their complements are ligated. The GMA beads are washed and the loaded beads are concentrated by FACS sorting, using the fluores-cently labelled cDNAs to identify loaded GMA beads. The isolated beads are treated with Pac I to remove the fluorescent label, after which the beads are heated in an NaOH solution using conventional protocols to remove the non-covalently bound strand. After several washes the GMA beads are ready for competitive hybridization.

EXAMPLE 3

Isolation and Identification of Up-Regulated and Down-Regulated Genes in Yeast Exposed to Different Growth Conditions In this example, mRNA is extracted from cells of each culture and two populations of labeled polynucleotides are produced by a single round of poly(dT) primer extension by a reverse transcriptase in the presence of fluorescently label nucleoside triphosphates. Equal amounts of each of the labeled polynucleotides are then combined with the GMA beads of Example 1 carrying the reference DNA population for competitive hybridization, after which the beads are analyzed by FACS and those in the off-diagonal regions are accumulated for MPSS analysis.

Fluorescent nucleoside triphosphates Cy3-dUTP or Cy5-dUTP (Amersham) are incorporated into cDNAs during reverse transcription of 1.25 $\mu$g of poly(A)⁺ RNA obtained as described in Example 1 using a poly(dT)$_{16}$ primer in separate reactions. After heating the primer and RNA to 70° C. for 10 min, the reaction mixture is transferred to ice and a premixed solution, consisting of 200 U Superscript II (Gibco), buffer, deoxyribonucleoside triphosphates, and fluorescent nucleoside triphosphates are added to give the following concentrations: 500 $\mu$M for dATP, dCTP, and dGTP; 200 $\mu$M for dTTP; and 100 mM each for Cy3-dUTP or Cy5-dUTP. After incubation at 42° C. for 2 hours, unincorporated fluorescent nucleotides are removed by first diluting the reaction mixture with 470 $\mu$l of 10 mM tris-HCl (pH 8.0)/1 mM EDTA and then subsequently concentrating to about 5$\mu$l using a Centricon-30 concentrator (Amicon). Purifed labeled cDNA from both reactions is combined and resuspended in 11 $\mu$l of 3.5 ×SSC containing 10 $\mu$g poly (dA) and 0.3 $\mu$l of 10% SDS. Prior to hybridization the solution is boiled for 2 min and allow to cool to room temperature, after which it is applied to the GMA beads and incubated for about 8–12 hours at 62° C. After washing twice in 2× SSC and 0.2% SDS, the GMA beads are resuspended in NEB-2 buffer (New England Biolabs, Beverly, Mass.) and loaded in a Coulter EPICS Elite ESP flow cytometer for analysis and sorting. In a two dimensional fluorecence intensity contour plot, the GMA beads generate a pattern as shown in FIG. 1a. Sorting parameters are set as shown in FIG. 1b so that GMA beads in the off-diagonal regions (112) are sorted and collected for MPSS analysis.

The labeled cDNA strands are melted from the GMA beads and removed by centrifugation. After several washes, a primer is annealed to the primer binding site shown in Formula I and extended in a conventional polymerization reaction to reconstitute the double stranded DNAs on the GMA beads which include the Dpn II site, described above. After digestion with Dpn II, beads loaded with tag-cDNA conjugates are placed in an instrument for MPSS analysis, as described in Albrecht et al (cited above).

The top strands of the following 16 sets of 64 encoded adaptors (SEQ ID NO: 10 through SEQ ID NO: 25) are each separately synthesized on an automated DNA synthesizer (model 392 Applied Biostems, Foster City) using standard methods. The bottom strand, which is the same for all adaptors, is synthesized separately then hybridized to the respective top strands:

| SEQ ID NO. | Encoded Adaptor |
|---|---|
| 10 | 5'-pANNNTACAGCTGCATCCCttggcgctgagg<br>pATGCACGCGTAGGG-5' |
| 11 | 5'-pNANNTACAGCTGCATCCCtgggcctgtaag<br>pATGCACGCGTAGGG-5' |
| 12 | 5'-pCNNNTACAGCTGCATCCCttgacgggtctc<br>pATGCACGCGTAGGG-5' |
| 13 | 5'-pNCNNTACAGCTGCATCCCtgcccgcacagt<br>pATGCACGCGTAGGG-5' |
| 14 | 5'-pGNNNTACAGCTGCATCCCttcgcctcggac<br>pATGCACGCGTAGGG-5' |
| 15 | 5'-pNGNNTACAGCTGCATCCCtgatccgctagc<br>pATGCACGCGTAGGG-5' |
| 16 | 5'-pTNNNTACAGCTGCATCCCttccgaacccgc<br>pATGCACGCGTAGGG-5' |
| 17 | 5'-pNTNNTACAGCTGCATCCCtgaggggatag<br>pATGCACGCGTAGGG-5' |
| 18 | 5'-pNNANTACAGCTGCATCCCttcccgctacac<br>pATGCACGCGTAGGG-5' |
| 19 | 5'-pNNNATACAGCTGCATCCCtgactcccgag<br>pATGCACGCGTAGGG-5' |
| 20 | 5'-pNNCNTACAGCTGCATCCCtgtgttgcgcgg<br>pATGCACGCGTAGGG-5' |
| 21 | 5'-pNNNCTACAGCTGCATCCCtctacagcagcg<br>pATGCACGCGTAGGG-5' |
| 22 | 5'-pNNGNTACAGCTGCATCCCtgtcgcgtcgtt<br>pATGCACGCGTAGGG-5' |
| 23 | 5'-pNNNGTACAGCTGCATCCCtcggagcaacct<br>pATGCACGCGTAGGG-5' |
| 24 | 5'-pNNTNTACAGCTGCATCCCtggtgaccgtag<br>pATGCACGCGTAGGG-5' |
| 25 | 5'-pNNNTTACAGCTGCATCCCtcccctgtcgga<br>pATGCACGCGTAGGG-5' | where N is any of dA, dC, dG, or dT; p is a phosphate group; and the nucleotides indicated in lower case letters are the 12-mer oligonucleotide tags. Each tag differs from every other by 6 nucleotides. Equal molar quantities of each adaptor are combined in NEB #2 restriction buffer (New England Biolabs, Beverly, Mass.) to form a mixture at a concentration of 1000 pmol/µL.

Each of the 16 tag complements are separately synthesized as amino-derivatized oligonucleotides and are each labelled with a fluorescein molecule (using an NHS-ester of fluorescein, available from Molecular Probes, Eugene, Oreg.) which is attached to the 5' end of the tag complement through a polyethylene glycol linker (Clonetech Laboratories, Palo Alto, Calif.). The sequences of the tag complements are simply the 12-mer complements of the tags listed Ligation of the adaptors to the target polynucleotide is carried out in a mixture consisting of 5 µl beads (20 mg), 3 µL NEB 10× ligase buffer, 5 µL adaptor mix (25 nM), 2.5 µL NEB T4 DNA ligase (2000 units/µL), and 14.5 µL distilled water. The mixture is incubated at 16° C. for 30 minutes, after which the beads are washed 3 times in TE (pH 8.0).

After centrifugation and removal of TE, the 3' phosphates of the ligated adaptors are removed by treating the polynucleotide-bead mixture with calf intestinal alkaline phosphatase (CIP) (New England Biolabs, Beverly, Mass.), using the manufacturer's protocol. After removal of the 3' phosphates, the CIP may be inactivated by proteolytic digestion, e.g. using Pronase™ (available form Boeringer Mamiem, Indianapolis, Ind.), or an equivalent protease, with the manufacturer's protocol. The polynucleotide-bead mixture is then washed, treated with a mixture of T4 polynucleotide kinase and T4 DNA ligase (New England Biolabs, Beverly, Mass.) to add a 5' phosphate at the gap between the target polynucleotide and the adaptor, and to complete the ligation of the adaptors to the target polynucleotide. The bead-polynucleotide mixture is then washed in TE.

Separately, each of the labelled tag complements is applied to the polynucleotide-bead mixture under conditions which permit the formation of perfectly matched duplexes only between the oligonucleotide tags and their respective complements, after which the mixture is washed under stringent conditions, and the presence or absence of a fluorescent signal is measured. Tag complements are applied in a solution consisting of 25 nM tag complement 50 mM NaCl, 3 mM Mg, 10 mM Tris-HCI (pH 8.5), at 20° C., incubated for 10 minutes, then washed in the same solution (without tag complement) for 10 minute at 55° C.

After the four nucleotides are identified as described above, the encoded adaptors are cleaved from the polynucleotides with Bbv I using the manufacturer's protocol. After an initial ligation and identification, the cycle of ligation, identification, and cleavage is repeated three times to give the sequence of the 16 terminal nucleotides of the target polynucleotide.

Figure 2:
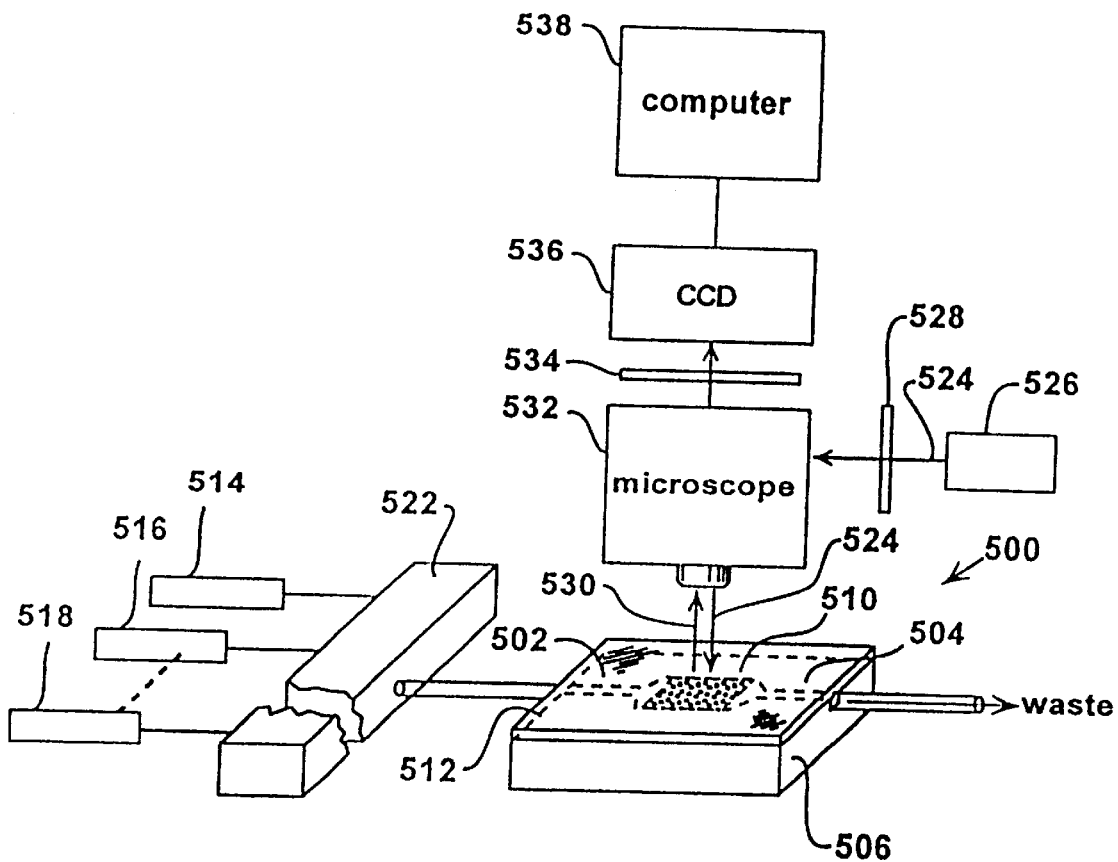
FIG. 2 is a schematic representation of a flow chamber and detection apparatus for observing a planar array of microparticles loaded with restriction fragments for sequencing.

Preferably, analysis of the hybridized encoded adaptors takes place in an instrument which i) constrains the loaded microparticles to be disposed in a planar array in a flow chamber, ii) permits the programmed delivery of process reagents to the flow chamber, and iii) detects simultaneously optical signals from the array of microparticles. Such a preferred instrument is shown diagrammatically in FIG. 2, and more fully disclosed in Bridgham et al, International patent application PCTIUS98111224. Briefly, flow chamber (500) is prepared by etching a cavity having a fluid inlet (502) and outlet (504) in a glass plate (506) using standard micromachining techniques, e.g. Ekstrom et al, International patent application PCT/SE91/00327; Brown, U.S. Pat. No. 4,911,782; Harrison et al, Anal. Chem. 64: 1926–1932 (1992); and the like. The dimension of flow chamber (500) are such that loaded microparticles (508), e.g. GMA beads, may be disposed in cavity (510) in a closely packed planar monolayer of 100–200 thousand beads. Cavity (510) is made into a closed chamber with inlet and outlet by anodic bonding of a glass cover slip (512) onto the etched glass plate (506), e.g. Pomerantz, U.S. Pat. No. 3,397,279. Reagents are metered into the flow chamber from syringe pumps (514 through 520) through valve block (522) controlled by a microprocessor as is commonly used on automated DNA and peptide synthesizers, e.g. Bridgham et al, U.S. patent 4,668,479; Hood et al, U.S. Pat. No. 4,252,769; Barstow et al, U.S. Pat. No. 5,203,368; Hunkapiller, U.S. Pat. No. 4,703,913; or the like.

Three cycles of ligation, identification, and cleavage are carried out in flow chamber (500) to give the sequences of 12 nucleotides at the termini of each of appoximately 100,000 fragments. Nucleotides of the fragments are identified by hybridizing tag complements to the encoded adaptors as described above. Specifically hybridized tag complements are detected by exciting their fluorescent labels with illumination beam (524) from light source (526), which may be a laser, mercury arc lamp, or the like. Illumination beam (524) passes through filter (528) and excites the fluorescent labels on tag complements specifically hybridized to encoded adaptors in flow chamber (500). Resulting fluorescence (530) is collected by confocal microscope (532), passed through filter (534), and directed to CCD camera (536), which creates an electronic image of the bead array for processing and analysis by workstation (538). Preferably, after each ligation and cleavage step, the cDNAs are treated with PronaseTM or like enzyme. Encoded adaptors and T4 DNA ligase (Promega, Madison, WIS.) at about 0.75 units per μL are passed through the flow chamber at a flow rate of about 1–2 μL per minute for about 20–30 minutes at 16° C., after which 3' phosphates are removed from the adaptors and the cDNAs prepared for second strand ligation by passing a mixture of alkaline phosphatase (New England Bioscience, Beverly, Mass.) at 0.02 units per pIL and T4 DNA kinase (New England Bioscience, Beverly, Mass.) at 7 units per pL through the flow chamber at 37° C. with a flow rate of 1–2 μL per minute for 15–20 minutes. Ligation is accomplished by T4 DNA ligase (.75 units per mL, Promega) through the flow chamber for 20-30 minutes. Tag complements at 25 DM concentration are passed through the flow chamber at a flow rate of 1–2 μL per minute for 10 minutes at 20° C., after which fluorescent labels carried by the tag complements are illuminated and fluorescence is collected. The tag complements are melted from the encoded adaptors by passing hybridization buffer through the flow chamber at a flow rate of 1–2 μL per minute at 55° C. for 10 minutes. Encoded adaptors are cleaved from the cDNAs by passing Bbv I (New England Biosciences, Beverly, MASS.) at 1 unit/μL at a flow rate of 1–2 μL per minute for 20 minutes at 37° C.

EXAMPLE 4

FACS Analysis of Microparticles Loaded with Different Ratios of DNAs Labeled with Fluorescein and CYS In this example, the sensitivity of detecting different ratios of differently labeled cDNAs was tested by constructing a reference DNA population consisting of a single clone and then competitively hybridizing to the reference DNA population different ratios of complementary strands labeled with different fluorescent dyes. The reference DNA population consisted of a cDNA clone, designated "88.11,"which is an 87-basepair fragment of an expressed gene of the human monocyte cell line THP-1, available from the American Type Culture Collection (Rockville, Md.) under accession number TIB 202. The nucleotide sequence of 88.11 has a high degree of homology to many entries in the GenBank Expressed Sequence Tag library, e.g. gb AA830602 (98%). The reference DNA population, which consisted of only 88.11 cDNA, was prepared as described in Example 1, with the exception that a special population of microparticles was prepared in which all microparticles had the same tag complement attached. The corresponding oligonucleotide tag was attached to the 88.11 cDNA. Thus, only monospecific populations of tags and tag complements were involved in the experiment. After competitive hybridization, the loaded microparticles were analyzed on a Cytomation, Inc. (Ft. Collins, Colo.) FACS instrument as described above.

88.11 cDNA was also cloned into a vector identical to that of Example 1 (330 of FIG. 3b), except that it did not contain tag 336. 10 μg of vector DNA was linearized by cleaving to completion with Sau 3A, an isoschizomer of Dpn II (342 of FIG. 3b), after which two 1 μg aliquots of the purified linear DNA were taken. From each 1 μg aliquot, about 20 μg of labeled single stranded DNA product was produced by repeated cycles of linear amplification using primers specific for primer binding site 332. In one aliquot, product was labeled by incorporation of rhodamine R110 labeled dUTP (PE Applied Biosystems, Foster City, Calif.); and in the other aliquot, product was labeled by incorporation of CY5-labeled dUTP (Amersham Corporation, Arlington Heights, Ill.). Quantities of the labeled products were combined to form seven 5 μg amounts of the two products in ratios of 1:1, 2:1, 1:2, 4:1, 1:4, 8:1, and 1:8. The 5 μg quantities of labeled product were seperately hybridized to 1.6×10$^5$ microparticles (GMA beads with 88.11 cDNA attached) overnight at 65° C. in 50 μ4×SSC with 0.2% SDS, after which the reaction was quenched by diluting to 10 ml with ice-cold TE/Tween buffer (defined above). The loaded microparticles were centrifuged, washed by suspending in 0.5 ml 1×SSC with 0.2% SDS for 15 min at 65° C., centrifuged, and washed again by suspending in 0.5 ml 0.1×SSC with 0.2% SDS for 15 min at 55° C. After the second washing, the microparticles were centrifuged and resuspended in 0.5 ml TE/Tween solution for FACS analysis.

Figure 5A:
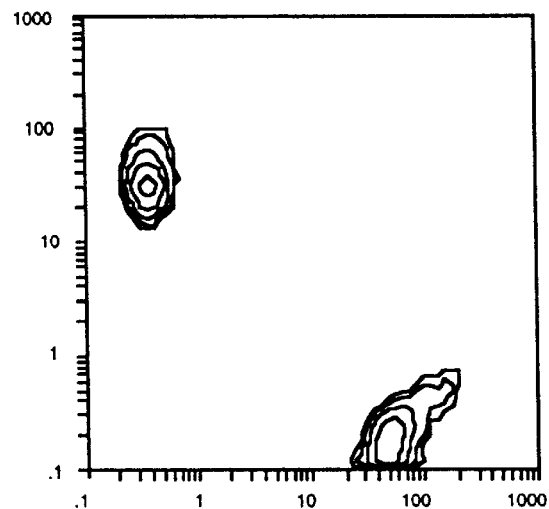
FIGS. 5a–e illustrate flow analysis data of microparticles carrying predetermined ratios of two differently labeled cDNAs.
Figure 5B:
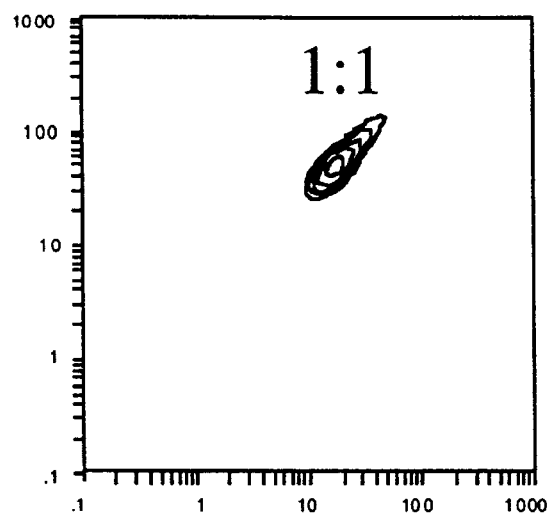
Figure 5C:
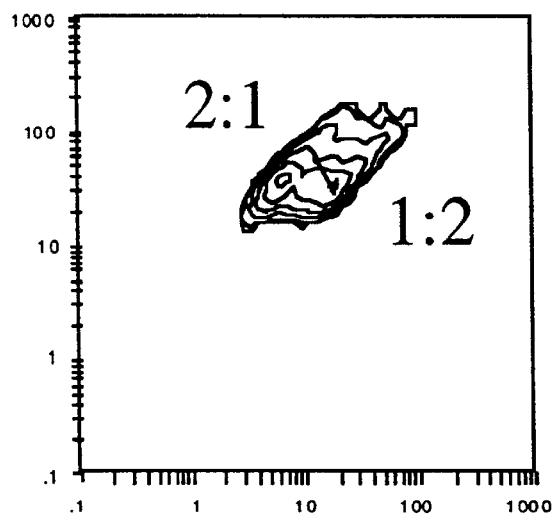
Figure 5D:
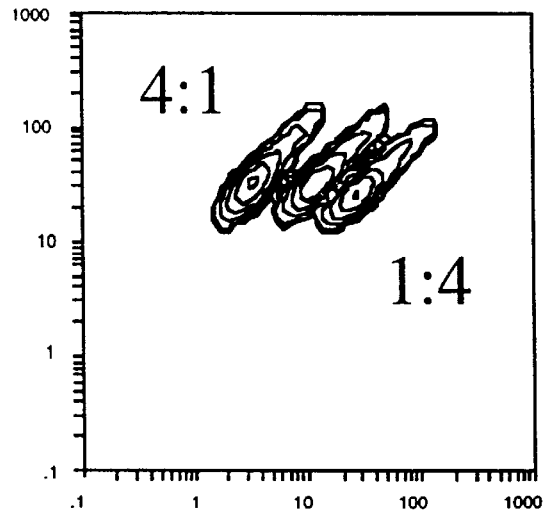
Figure 5E:
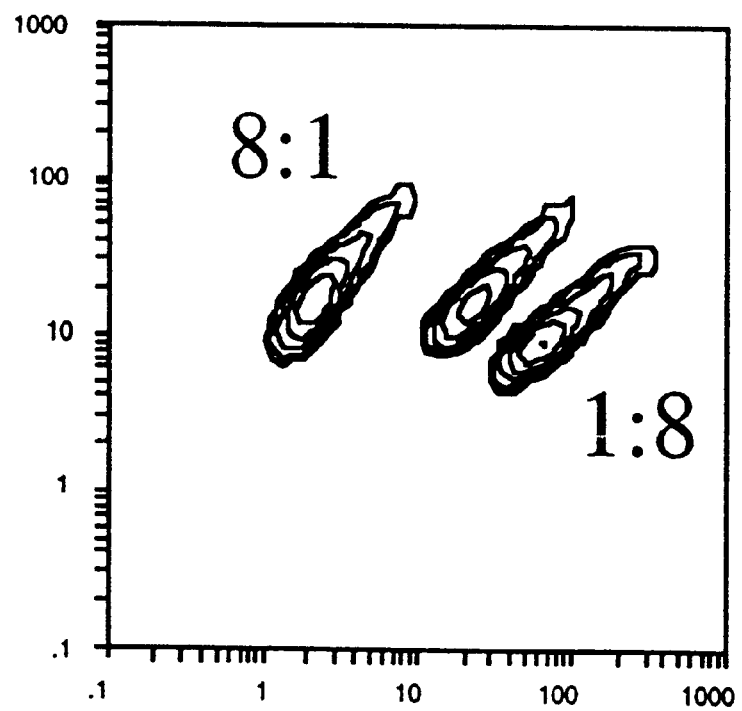

The results are shown in FIGS. 5a–5e, where in each Figure the vertical axis corresponds to CY5 fluorescence and the horizontal axis corresponds to rhodamine R110 fluorescence. In FIG. 5a, a population of microparticles were combined that had either all R110-labeled DNA or all CY5-labeled DNA hybridized to the complementary reference strands. Contours 550 and 552 are clearly distinguished by the detection system of the FACS instrument and microparticles of both populations produce readily detectable signals. FIG. 5b illustrates the case where the R110- and CY5-labeled strands are hybridized in equal proportions. As expected, the resulting contour is located on the diagonal of the graph and corresponds to the position expected for non-regulated genes. FIGS. 5c through 5e show the analysis of three pairs of competitive hybridizations: i) R110- and CY5-labeled strands hybridized in a 2:1 concentration ratio and a 1:2 concentration ratio, ii) R110- and CY5-labeled strands hybridized in a 4:1 concentration ratio and a 1:4 concentration ratio, and iii) RI 10- and CY5-labeled strands hybridized in an 8:1 concentration ratio and a 1:8 concentration ratio. The data of FIG. 5c suggest that genes up-regulated or down-regulated by a factor of two are detectable in the present embodiment, but that significant overlap may exist between signals generated by regulated and non-regulated genes. FIGS. 5d and 5e suggest that genes up-regulated or down-regulated by a factor of four or higher are readily detectable over non-regulated genes.

EXAMPLE 5

FACS Analysis of Differentially Expressed Genes from Stimulated and Unstimulated THP-1 Cells In this example, a reference DNA population attached to microparticles was constructed from cDNA derived from THP-1 cells stimulated as indicated below. Equal concentrations of labeled cDNAs from both stimulated and unstimulated THP-1 cells were then competitively hybridized to the reference DNA population, as described in Example 1, and the microparticles carrying the labeled cDNAs were analyzed by a FACS instrument. THP-1 cells were stimulated by treatnent with phorbol 12-myristate 13-acetate (PMA) and lipopolysaccharide (LPS).

THP-1 cells were grown in T-165 flasks (Costar, No. 3151) containing 50 ml DMEM/F12 media (Gibco, No. 11320-033) supplemented with 10% fetal bovine serum (FBS)(Gibco, No. 26140-038), 100 units/ml penicillin, 100

μg/ml streptomycin (Gibco, No. 15140-122), and 0.5 μMl β-mercaptoethanol (Sigma, No. M3148). Cultures were seeded with 1 ×10$^5$ cells/ml and grown to a maximal density of 110$^6$. Doubling time of the cell populations in culture was about 36 hours. Cells were treated with PMA as follows: Cells from a flask (about 5×10$^7$ cells) were centrifuged (Beckman model GS-6R) at 1200 rpm for 5 minutes and resuspended in 50 ml of fresh culture media (without antibiotics) containing 5 μd of 1.0 mM PMA (Sigma, No. P-8139) in DMSO (Gibco No. 21985023) or 5 μl A DMSO (for the unstimulated population), after which the cells were cultured for 48 hours. Following the 48 hour incubation, media and non-adherent cells were aspirated from the experimental flask (i.e. containing stimulated cells) and fresh media (without antibiotics) was added, the fresh media containing 10 μl of 5 mg/ml LPS (Sigma, No. L-4130) in phosphate buffered saline (PBS). The culture of unstimulated cells was centrifuged (Beckman model GS-6R) at 1200 rpm for 5 minutes at 4° C. so that a pellet formed which was then resuspended in 50 ml of fresh growth media containing 10 μl PBS. Both the cultures of stimulated and unstimulated cells were incubated at 37° C. for four hours, after which cells were harvested as follows: Media was aspirated from the cultures and adherent cells were washed twice with warm PBS, after which 10 ml PBS was added and the cells were dislodged with a cell scaper. The dislodged cells were collected and their concentration was determined with a hemocytometer, after which they were centrifuged (Beckman model GS-6R) at 1200 rpm for 5 minutes to form a pellet which was used immediately for RNA extraction.

MRNA was extracted from about 5 ×10$^6$ cells using a FastTrack 2.0 kit (No. K1593-02, Invitrogen, Inc. San Diego, Calif.) for isolating mRNA. The manufacturer's protocol was followed without significant alterations. A reference DNA population attached to microparticles was constructed from mRNA extracted from stimulated cells, as described in Example 1. Separate cDNA libaries were constructed from mRNA extracted from stimulated and unstimulated cells. The vectors used for the libraries were identical to that of Example 1, except that they did not contain oligonucleotide tags (336 of FIG. 3b). Following the protocol of Example 4, approximately 2.5 μg of rhodamine R110-labeled single stranded DNA was produced from the cDNA library derived from stimulated cells, and approximately 2.5 μg of CY5-labeled single stranded DNA was produced from the cDNA library derived from unstimulated cells. The two 2.5 μg aliquots were mixed and competitively hybridized to the reference DNA on 9.34×10$^5$ microparticles. The reaction conditions and protocol was as described in Example 4.

Figure 6:
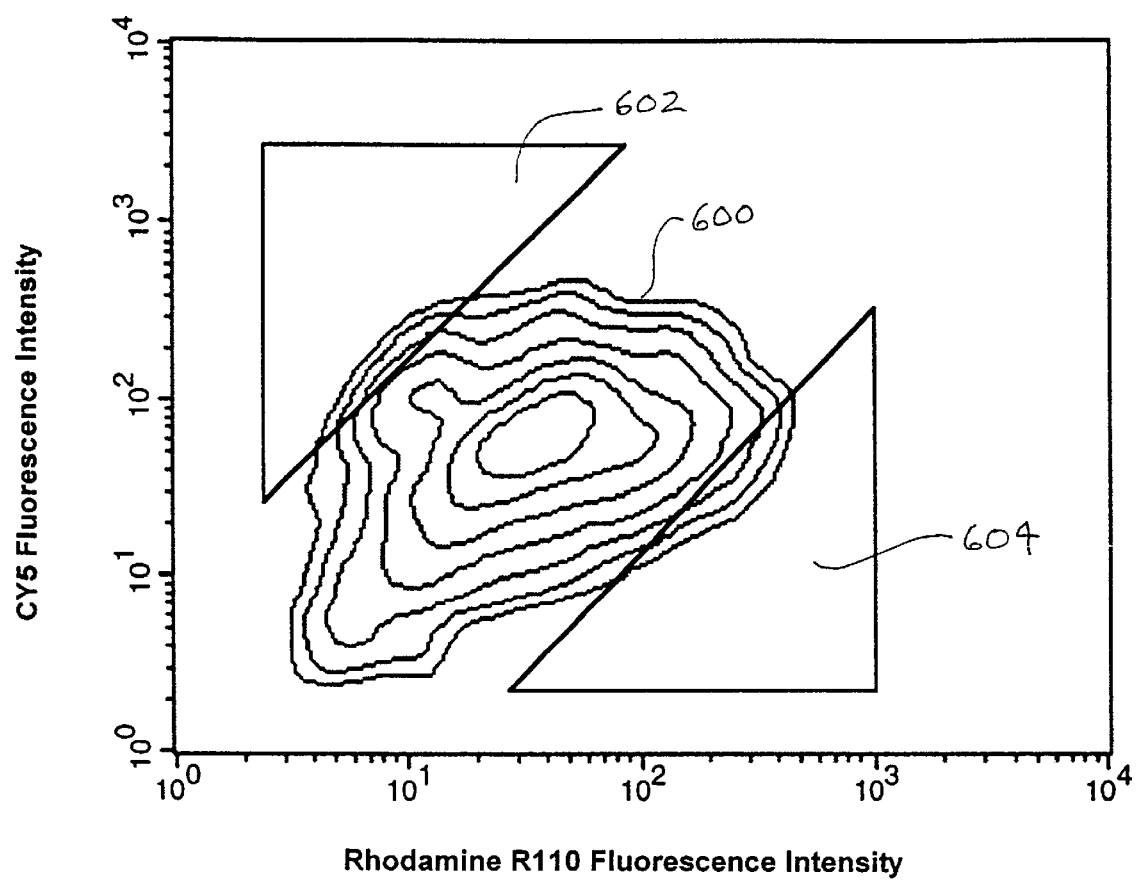
FIG. 6 illustrates flow analysis data of microparticles carrying differently labeled cDNAs from stimulated and unstimulated THP-1 cells.

After hybridization, the microparticles were sorted by a Cytomation, Inc. MoFlo FACS instrument as described above. FIG. 6 contains a conventional FACS contour plot 600 of the frequencies of microparticles with different fluorescent intensity values for the two fluorescent dyes. Appoximately 10,000 microparticles corresponding to up-regulated genes (sort window 602 of FIG. 6) were isolated, and approximately 12,000 microparticles corresponding to down-regulated genes (sort window 604 of FIG. 6) were isolated. After melting off the labeled strands, as described above, the cDNAs carried by the microparticles were amplified using a commericial PCR cloning kit (Clontech Laboratories, Palo Alto, Calif.), and cloned into the manufacturer's recommended cloning vector. After transformation, expansion of a host culture, and plating, 87 colonies of up-regulated cDNAs were picked and 73 colonies of down-regulated cDNAs were picked. cDNAs carried by plasmids extracted from these colonies were sequenced entional protocols on a PE Applied Biosystems model 373 automated DNA The identified sequences are listed in Tables 1 and 2.

TABLE 1

Up-Regulated Genes

| No. Copies | Description | GenBank Indentifier |
|---|---|---|
| 19 | LD78/MIP-1 | HUMCKLD78 |
| 16 | TNF-inducible (TSF-6) mRNA | HUMTSG6A |
| 15 | GRO-γ (MIP-2β) | HUMGROG5 |
| 6 | GRO-β (MIP-2α) | HUMGROB |
| 6 | act-2 | HUMACT2A |
| 4 | guanylate binding protein isoform I (GBP-2) | HUMGBP1 |
| 4 | spermidine/spermin N1-acetyltransferase | HUMSPERMNA |
| 4 | adipocyte lipid-binding protein | HUMALBP |
| 3 | fibronectin | HSFIB1 |
| 3 | interleukin-8 | HSMDNCF |
| 1 | insulin-like growth factor binding protein 3 | HSIGFBP3M |
| 1 | interferon-γ inducible eariy response gene | HSINFGER |
| 1 | type IV collangenase | |
| 1 | cathepsin L | HSCATHL |
| 1 | EST | |
| 1 | EST | |
| 1 | genomic/EST | HSAC002079 |

TABLE 2

Down-Regulated Genes

| No. Copies | Description | GenBank Indentifier |
|---|---|---|
| 16 | elongation factor 1 | HSEF1AC |
| 4 | ribosomal protein S3a/v-fos tranf. effector | HUMFTE1A |
| 6 | ribosomal protein S7 | HUMRPS17 |
| 2 | translationally controlled tumor protein | HSTUMP |
| 3 | 23 kD highly basic protein | HS23KDHBP |
| 2 | laminin receptor | HUMLAMR |
| 2 | cytoskeletal gamma-actin | HSACTCGR |
| 2 | ribosomal protein L6 | HSRPL6AA |
| 2 | ribosomal protein L10 | HUMRP10A |
| 2 | ribosomal protein L21 | HSU14967 |
| 2 | ribosomal protein S27 | HSU57847 |
| 1 | ribosomal protein L5 | HSU14966 |
| 1 | ribosomal protein L9 | HSU09953 |
| 1 | ribosomal protein L17 | HSRPL17 |
| 1 | ribosomal protein L30 | HSRPL30 |
| 1 | ribosomal protein L38 | HSRPL38 |
| 1 | ribosomal protein S8 | HSRPS8 |
| 1 | ribosomal protein S13 | HSRPS13 |
| 1 | ribosomal protein S18 | HSRPS18 |
| 1 | ribosomal protein S20 | HUMRPS20 |
| 1 | acidic ribosomal phosphoprotein PO | HUMPPARP0 |
| 1 | 26S proteasome subunit p97 | HUM26SPSP |
| 1 | DNA-binding protein B | HUMAAE |
| 1 | T-cell cyclophilin | HSCYCR |
| 1 | interferon inducible 6-26 mRNA | HSIFNIN4 |
| 1 | hematopoetic proteoglycan core protein | HSHPCP |
| 1 | fau | HSFAU |
| 1 | beta-actin | HSACTB |
| 1 | nuclear enc. mito. serine hydroxymethyltrans. | HUMSHMTB |
| 1 | mito. cytochrome c oxidase subunit II | HUMMTCDK |
| 1 | genomic | W92931 |
| 1 | EST | W84529 |
| 1 | EST | AA933890 |
| 1 | EST | AA206288 |
| 1 | EST | AA649735 |
| 1 | EST | N34678 |
| 1 | EST | AA166702 |
| 1 | EST | AA630799 |
| 3 | genomic | AA630797 |

We claim:

1. A method of analyzing relative gene expression in a plurality of different cells or tissues, the method comprising the steps of:

providing a reference DNA population of DNA sequences attached to septerate solid phase supports in clonal subpopulations;

providing a population of polynucleotides of expressed genes from each of the plurality of different cells or tissues, the polynucleotides of expressed genes from different cells or tissues having a different light-generating label and the polynucleotides of expressed genes from the same cells or tissues having the same light-generating label; and competitively hybridizing the populations of polynucleotides of expressed genes from each of the plurality of different cells or tissues with the reference DNA population to form duplexes between the DNA sequences of the reference DNA population and polynucleotides of each of the different cells or tissues such that polynucleotides from the same gene of the different cells or tissues hybeidize with the same complementary sequence of the reference DNA population and such that such polynucleotides are present in duplexes on each of the solid phase supports in ratios directly related to the relative expression of their corresponding genes in the different cells or tissues; and sorting each solid phase support according to a relative optical signal generated by the light-generating labels of the duplexes attached thereto.

2. The method of claim 1 wherein said reference DNA population is derived from said expressed genes of said plurality of different cells or tissues being analyzed.

3. The method of claim 2 wherein said different light-generating labels are different fluorescent labels.

4. The method of claim 3 wherein said population of polynucleotides of expressed genes are populations of cDNAs.

5. The method of claim 4 further comprising the steps of:

accumulating in a seperate vessel each said solid phase support having said relative optical signal with a value within one or more predetermined ranges of values corresponding to a difference in gene expression among said plurality of different cells or tissues; and identifying said polynucleotides on each of said solid supports by determining a nucleotide sequence of a portion of each of said polynucleotides.

6. The method of claim 5 wherein said relative optical signal is a ratio of fluorescence intensities and wherein said plurality of different cells or tissues is two.

7. The method of claim 6 wherein said portion of said polynucleotides is a sequence of at least ten nucleotides.

8. The method of claim 6 wherein said step of identifying includes simultaneous sequencing of at least ten thousand of said polynucleotides by massively parallel signature sequencing.

9. A method of isolating polynucleotides derived from genes differentially expressed in a plurality of different cells or tissues, the method comprising the steps of:

providing a reference DNA population of DNA sequences attached to separate microparticles in clonal subpopulations;

providing a population of polynucleotides derived from genes expressed in each of the plurality of different cells or tissues, each polynucleotide having a light-generating label capable of generating an optical signal indicative of the cells or tissues from which it is derived;

competitively hybridizing the populations of polynucleotides of genes expressed in each of the plurality of different cells or tissues with the reference DNA population to form duplexes between the DNA sequences of the reference DNA population and polynucleotides from each of the different cells or tissues such that polynucleotides from the same gene of the different cells or tissues hybridize with the same complementary sequence of the reference DNA population and such that such polynucleotides are present in dupleses on each of the microparticles in ratios directly related to the relative expression of their corresponding genes in the different cells or tissues; and isolating polynucleotides corresponding to genes differentially expressed in the different cells or tissues by sorting microparticles in accordance with the optical signals generated by the populations of polynucleotides hybridized thereto.

10. The method of claim 9 wherein said reference DNA population is derived from genes expressed in the plurality of different cells or tissues being analyzed.

11. The method of claim 10 wherein said plurality of different cells or tissues is two and wherein said optical signal is a fluorescent signal.

12. The method of claim 11 wherein said populations of polynucleotides are labeled with different fluorescent labels.

13. The method of claim 12 wherein said populations of polynucleotides are populations of cDNAs.

14. The method of claim 13 wherein said step of isolating includes sorting said microparticles in accordance with the ratio of fluorescence intensities generated by said populations of cDNAs hybridized thereto.

15. The method of claim 14 wherein said step of isolating includes sorting said microparticle with a fluorescence-activated cell sorter.

16. The method of claim 15 further including the step of identifying said isolated cDNAs by determining a nucleotide sequence of a portion of each said isolated cDNA.

* * * * *

SEQUENCE LISTING

<160> NUMBER OF SEQ ID NOS: 25

<210> SEQ ID NO 1
<211> LENGTH: 89
<212> TYPE: DNA
<213> ORGANISM: Artificial Sequence
<220> FEATURE:
<221> NAME/KEY: Unsure.
<222> LOCATION: 71-76
<223> OTHER INFORMATION: a, c, g, t, or u

<400> SEQUENCE: 1
agaattcggg ccttaattaa dddddddddd dddddddddd dddddddddd        50
ddgggcccgc ataagtcttc nnnnnnggat ccgagtgat                    89

<210> SEQ ID NO 2
<211> LENGTH: 41
<212> TYPE: DNA
<213> ORGANISM: Artificial Sequence
<220> FEATURE:
<221> NAME/KEY: Primer.
<222> LOCATION: n.a.
<223> OTHER INFORMATION: Exemplary primer for reverse transcription of
      mRNA.

<400> SEQUENCE: 2
gacatgctgc attgagacga ttcttttttt tttttttttt v                 41

<210> SEQ ID NO 3
<211> LENGTH: 52
<212> TYPE: DNA
<213> ORGANISM: Artificial Sequence
<220> FEATURE:
<221> NAME/KEY: Unsure.
<222> LOCATION: 42-45, 50-52
<223> OTHER INFORMATION: a, c, g, t, or u

<400> SEQUENCE: 3
gacatgctgc attgagacga ttcttttttt tttttttttt vnnnngatcn        50 nn                                                            52

<210> SEQ ID NO 4
<211> LENGTH: 37
<212> TYPE: DNA
<213> ORGANISM: Artificial Sequence
<220> FEATURE:
<221> NAME/KEY: Unsure.
<222> LOCATION: 34-37
<223> OTHER INFORMATION: a, c, g, t, or u

<400> SEQUENCE: 4
gcattgagac gattcttttt tttttttttt ttvnnnn                      37

<210> SEQ ID NO 5
<211> LENGTH: 73
<212> TYPE: DNA
<213> ORGANISM: Artificial Sequence
<220> FEATURE:
<221> NAME/KEY: Unsure.
<222> LOCATION: 62-67
<223> OTHER INFORMATION: a, c, g, t, or u

<400> SEQUENCE: 5
ttaattaagg adddddddddd dddddddddd dddddddddd dddgggcccg       50

```
cataagtctt cnnnnnngga tcc                                          73

<210> SEQ ID NO 6
<211> LENGTH: 63
<212> TYPE: DNA
<213> ORGANISM: Artificial Sequence
<220> FEATURE:
<221> NAME/KEY: n.a.
<222> LOCATION: Attached to solid phase support.
<223> OTHER INFORMATION: No additional information.

<400> SEQUENCE: 6
ccchhhhhhh hhhhhhhhhh hhhhhhhhhh hhhhtccttt aattaactgg             50
tctcactgtc gca                                                     63

<210> SEQ ID NO 7
<211> LENGTH: 18
<212> TYPE: DNA
<213> ORGANISM: Artificial Sequence
<220> FEATURE:
<221> NAME/KEY: Adaptor.
<222> LOCATION: n.a.
<223> OTHER INFORMATION: Preferably, contains fluorescent label.

<400> SEQUENCE: 7
gatcacgagc tgccagtc                                                18

<210> SEQ ID NO 8
<211> LENGTH: 22
<212> TYPE: DNA
<213> ORGANISM: Artificial Sequence
<220> FEATURE:
<221> NAME/KEY: Primer.
<222> LOCATION: n.a.
<223> OTHER INFORMATION: Exemplary forward primer.

<400> SEQUENCE: 8
agtgaattcg ggccttaatt aa                                           22

<210> SEQ ID NO 9
<211> LENGTH: 32
<212> TYPE: DNA
<213> ORGANISM: Artificial Sequence
<220> FEATURE:
<221> NAME/KEY: Primer.
<222> LOCATION: n.a.
<223> OTHER INFORMATION: Exemplary reverse primer.

<400> SEQUENCE: 9
ctacccgcgg ccgcggtcga ctctagagga tc                                32

<210> SEQ ID NO 10
<211> LENGTH: 30
<212> TYPE: DNA
<213> ORGANISM: Artificial Sequence
<220> FEATURE:
<221> NAME/KEY: Unsure.
<222> LOCATION: 2-4
<223> OTHER INFORMATION: a, c, g, t, or u

<400> SEQUENCE: 10
annntacagc tgcatccctt ggcgctgagg                                   30

<210> SEQ ID NO 11
<211> LENGTH: 30
<212> TYPE: DNA
<213> ORGANISM: Artificial Sequence
```

```
<220> FEATURE:
<221> NAME/KEY: Unsure.
<222> LOCATION: 1, 3-4
<223> OTHER INFORMATION: a, c, g, t, or u

<400> SEQUENCE: 11
nanntacagc tgcatccctg ggcctgtaag                                    30

<210> SEQ ID NO 12
<211> LENGTH: 30
<212> TYPE: DNA
<213> ORGANISM: Artificial Sequence
<220> FEATURE:
<221> NAME/KEY: Unsure.
<222> LOCATION: 2-4
<223> OTHER INFORMATION: a, c, g, t, or u

<400> SEQUENCE: 12
cnnntacagc tgcatccctt gacgggtctc                                    30

<210> SEQ ID NO 13
<211> LENGTH: 30
<212> TYPE: DNA
<213> ORGANISM: Artificial Sequence
<220> FEATURE:
<221> NAME/KEY: Unsure.
<222> LOCATION: 1, 3-4
<223> OTHER INFORMATION: a, c, g, t, or u

<400> SEQUENCE: 13
ncnntacagc tgcatccctg cccgcacagt                                    30

<210> SEQ ID NO 14
<211> LENGTH: 30
<212> TYPE: DNA
<213> ORGANISM: Artificial Sequence
<220> FEATURE:
<221> NAME/KEY: Unsure.
<222> LOCATION: 2-4
<223> OTHER INFORMATION: a, c, g, t, or u

<400> SEQUENCE: 14
gnnntacagc tgcatccctt cgcctcggac                                    30

<210> SEQ ID NO 15
<211> LENGTH: 30
<212> TYPE: DNA
<213> ORGANISM: Artificial Sequence
<220> FEATURE:
<221> NAME/KEY: Unsure.
<222> LOCATION: 1, 3-4
<223> OTHER INFORMATION: a, c, g, t, or u

<400> SEQUENCE: 15
ngnntacagc tgcatccctg atccgctagc                                    30

<210> SEQ ID NO 16
<211> LENGTH: 30
<212> TYPE: DNA
<213> ORGANISM: Artificial Sequence
<220> FEATURE:
<221> NAME/KEY: Unsure.
<222> LOCATION: 2-4
<223> OTHER INFORMATION: a, c, g, t, or u

<400> SEQUENCE: 16
tnnntacagc tgcatccctt ccgaacccgc                                    30
```

<210> SEQ ID NO 17
<211> LENGTH: 30
<212> TYPE: DNA
<213> ORGANISM: Artificial Sequence
<220> FEATURE:
<221> NAME/KEY: Unsure.
<222> LOCATION: 1, 3-4
<223> OTHER INFORMATION: a, c, g, t, or u

<400> SEQUENCE: 17
ntnntacagc tgcatccctg aggggatag                                30

<210> SEQ ID NO 18
<211> LENGTH: 30
<212> TYPE: DNA
<213> ORGANISM: Artificial Sequence
<220> FEATURE:
<221> NAME/KEY: Unsure.
<222> LOCATION: 1-2, 4
<223> OTHER INFORMATION: a, c, g, t, or u

<400> SEQUENCE: 18
nnantacagc tgcatccctt cccgctacac                                30

<210> SEQ ID NO 19
<211> LENGTH: 30
<212> TYPE: DNA
<213> ORGANISM: Artificial Sequence
<220> FEATURE:
<221> NAME/KEY: Unsure.
<222> LOCATION: 1-3
<223> OTHER INFORMATION: a, c, g, t, or u

<400> SEQUENCE: 19
nnnatacagc tgcatccctg actccccgag                                30

<210> SEQ ID NO 20
<211> LENGTH: 30
<212> TYPE: DNA
<213> ORGANISM: Artificial Sequence
<220> FEATURE:
<221> NAME/KEY: Unsure.
<222> LOCATION: 1-2, 4
<223> OTHER INFORMATION: a, c, g, t, or u

<400> SEQUENCE: 20
nncntacagc tgcatccctg tgttgcgcgg                                30

<210> SEQ ID NO 21
<211> LENGTH: 30
<212> TYPE: DNA
<213> ORGANISM: Artificial Sequence
<220> FEATURE:
<221> NAME/KEY: Unsure.
<222> LOCATION: 1-3
<223> OTHER INFORMATION: a, c, g, t, or u

<400> SEQUENCE: 21
nnnctacagc tgcatccctc tacagcagcg                                30

<210> SEQ ID NO 22
<211> LENGTH: 30
<212> TYPE: DNA
<213> ORGANISM: Artificial Sequence
<220> FEATURE:
<221> NAME/KEY: Unsure.
<222> LOCATION: 1-2, 4
<223> OTHER INFORMATION: a, c, g, t, or u -continued

```
<400> SEQUENCE: 22
nngntacagc tgcatccctg tcgcgtcgtt                                           30

<210> SEQ ID NO 23
<211> LENGTH: 30
<212> TYPE: DNA
<213> ORGANISM: Artificial Sequence
<220> FEATURE:
<221> NAME/KEY: Unsure.
<222> LOCATION: 1-3
<223> OTHER INFORMATION: a, c, g, t, or u

<400> SEQUENCE: 23
nnngtacagc tgcatccctc ggagcaacct                                           30

<210> SEQ ID NO 24
<211> LENGTH: 30
<212> TYPE: DNA
<213> ORGANISM: Artificial Sequence
<220> FEATURE:
<221> NAME/KEY: Unsure.
<222> LOCATION: 1-2, 4
<223> OTHER INFORMATION: a, c, g, t, or u

<400> SEQUENCE: 24
nntntacagc tgcatccctg gtgaccgtag                                           30

<210> SEQ ID NO 25
<211> LENGTH: 30
<212> TYPE: DNA
<213> ORGANISM: Artificial Sequence
<220> FEATURE:
<221> NAME/KEY: Unsure.
<222> LOCATION: 1-3
<223> OTHER INFORMATION: a, c, g, t, or u

<400> SEQUENCE: 25
nnnttacagc tgcatccctc ccctgtcgga                                           30
```